(12) United States Patent  (10) Patent No.: US 9,155,542 B2
Markarian  (45) Date of Patent: Oct. 13, 2015

(54) ARTHROSCOPIC METHOD AND APPARATUS FOR ROTATOR CUFF REPAIR

(76) Inventor: Gregory Markarian, Miami Beach, FL (US)

( * ) Notice: Subject to any disclaimer, the term of this patent is extended or adjusted under 35 U.S.C. 154(b) by 539 days.

(21) Appl. No.: 13/356,267

(22) Filed: Jan. 23, 2012

(65) Prior Publication Data

US 2013/0190871 A1 Jul. 25, 2013

(51) Int. Cl.
*A61F 2/08* (2006.01)
*A61B 17/16* (2006.01)
*A61B 17/04* (2006.01)

(52) U.S. Cl.
CPC ............ *A61B 17/16* (2013.01); *A61B 17/0401* (2013.01); *A61F 2/08* (2013.01); *A61F 2/0805* (2013.01); *A61F 2/0811* (2013.01); *A61B 17/1631* (2013.01); *A61B 17/1633* (2013.01); *A61B 17/1675* (2013.01); *A61B 2017/045* (2013.01); *A61B 2017/0496* (2013.01); *A61F 2002/0823* (2013.01); *A61F 2002/0864* (2013.01); *A61F 2002/0882* (2013.01)

(58) Field of Classification Search
CPC ....... A61F 2/08; A61F 2/0805; A61F 2/0811; A61F 2002/0823; A61F 2002/0829; A61F 2002/0817; A61F 2002/0882; A61B 17/1615; A61B 17/1617; A61B 17/1642; A61B 17/1684; A61B 17/1714; A61B 2017/1778; A44B 11/12; A44B 11/258; A44B 11/2588; A44B 11/2549; A44B 11/00; A44B 11/14; Y10T 24/3947; Y10T 24/3949; F16G 11/10; F16G 11/105
USPC .............. 623/13.11–13.2; 606/216, 218, 232; 254/264–270, 371; 160/178.2; 24/165, 24/166, 191, 178, 173
See application file for complete search history.

(56) References Cited

U.S. PATENT DOCUMENTS

| | | | | |
|---|---|---|---|---|
| 4,250,597 | A * | 2/1981 | Ford et al. | 24/132 R |
| 5,723,008 | A * | 3/1998 | Gordon | 606/75 |
| 5,766,186 | A | 6/1998 | Faraz et al. | |
| 6,471,715 | B1 | 10/2002 | Weiss | |
| 6,855,157 | B2 | 2/2005 | Foerster et al. | |
| 7,771,441 | B2 | 8/2010 | Cerundolo | |
| 2006/0241620 | A1 * | 10/2006 | Cerundolo | 606/72 |
| 2007/0270771 | A1 | 11/2007 | Ralph et al. | |

OTHER PUBLICATIONS

The International Search Report and the Written Opinion of the International Searching Authority, or the Declaration, Mailed May 31, 2013 for PCT/US13/22498, International filed: Jan. 22, 2013, Applicant: Dr. Gregory Markarian.
PCT Notification Transmittal and copy of International Preliminary Report on Patentability, Mailed Aug. 7, 2014 for PCT/US2013/022498, International filing date: Jan. 22, 2013, Applicant: Dr. Gregory Markarian.

* cited by examiner

*Primary Examiner* — Christopher D Prone
*Assistant Examiner* — Rokhaya Diop
(74) *Attorney, Agent, or Firm* — McAndrews, Held & Malloy, Ltd.

(57) ABSTRACT

An arthroscopic method for reattaching a rotator cuff tendon to a humeral head may include creating a trough in the top of the humeral head, creating a cavity in the lateral portion of the humeral head, creating one or more tunnels between the cavity and the trough, retrieving sutures affixed to a loose end of the tendon through the trough, at least one tunnel, and the cavity; and passing the sutures through a tensioning and securing device, which is then implanted in the cavity, and the sutures are variously pulled or released to pull, tension, or release the sutures until the tendon is secured in the trough. The trough is preferably created using a unique extendable, angled surgical burr.

9 Claims, 23 Drawing Sheets

ARTHROSCOPIC METHOD AND APPARATUS FOR ROTATOR CUFF REPAIR

RELATED APPLICATIONS

None.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present method and apparatus for rotator cuff repair generally relates to methods and devices for surgical repair of soft tissue damage. More specifically, the present method and apparatus-for rotator cuff repair relates to methods and devices for reattaching tendons to bone.

It has been estimated that over 15 million people in the United States alone are at risk from disability related to rotator cuff injuries. The rotator cuff is a group of four muscles in the shoulder: the supraspinatus; the infraspinatus; the teres minor; and the subscapularis. The supraspinatus extends over the top of the humerus, and is attached to the top of the humeral head by a tendon. This tendon can tear, and often tears away from the humeral head. These tears cause pain and limited mobility. Surgical repair of rotator cuff tears is common, but the surgical technique used to accomplish these repairs has changed significantly over time.

Historically, rotator cuff repairs have been performed in an open fashion. The traditional open approach involved a relatively large incision, e.g. 5 cm, and splitting of the deltoid to "open" the affected area for repair. Once open, the humeral head was exposed, and a burr and rongeur were typically used to create a trough in the top of the humeral head, exposing bone marrow on all sides and the bottom of the trough. A transosseous bone tunnel or tunnels were also created between the trough and the lateral cortex. The tendon was sutured, and the sutures passed through transosseous tunnel(s). The tendon was then pulled into the trough, and the sutures were typically tied over the lateral cortex for fixation.

The open approach is still described as the "gold standard" of rotator cuff repair because of the excellent functional results that rarely deteriorate over time. The trough provides excellent biological fixation between the tendon and the bone. Yet, a major disadvantage of the open technique is the required traumatic splitting of the deltoid. This often causes a long recovery time for patients, and can result in deltoid dehiscence and deltoid atrophy.

Over time, rotator cuff repair has evolved to include less invasive and traumatic approaches. A "mini-open" approach was developed that still involved an open incision and splitting of the deltoid to fix the tendon to the humeral head, but took an arthroscopic approach to other aspects of the repair. For example, in the mini-open approach, an arthroscope can be used to inspect the tear and surrounding anatomy. The tendon can also be released arthroscopically, and a subacromial bursectomy and decortication of the greater tuberosity performed. The tendon is typically fixed, however, using anchors or transosseous tunnels through a traditional open incision. Decortication of the humeral head is intended to promote a biological healing response, but is inferior to the creation of a trough.

Most recently, various techniques for purely arthroscopic rotator cuff repair have been developed. In these approaches, tendon fixation is also accomplished arthroscopically. These purely arthroscopic approaches rely on suture anchors implanted arthoscopically into the humeral head for fixation of the tendon. One disadvantage of the purely arthroscopic approaches is the technical complexity of such an operation. The most significant disadvantage of this approach, however, is that it lacks the biological healing associated with the tendon-to-trough healing of the open repair. Today's arthroscopic repair failures are commonly associated with bone, anchor, suture, or suture to tendon failure. Numerous refinements in suture techniques and anchor designs have been made in response, yet these refinements do not promote biological healing that may be crucial to obtaining lasting rotator cuff repairs.

BRIEF SUMMARY OF THE INVENTION

One embodiment of the present method and apparatus for rotator cuff repair involves an arthroscopic method for reattachment of a rotator cuff tendon to its footprint. The method comprises: arthroscopically affixing sutures to a loose end of a rotator cuff tendon; arthroscopically creating a trough in the top portion of the humeral head, arthroscopically creating a cavity in the humeral head, the cavity located below the top portion of the humeral head, the cavity extending into the humeral head in a direction substantially perpendicular to a lateral surface of the humeral head, the cavity having an opening in the lateral surface of the humeral head; arthroscopically creating at least one tunnel between the cavity and the trough; arthroscopically passing the sutures through the at least one tunnel and the cavity; positioning the tendon in the trough; passing the sutures through an adjustable tensioning and securing device configured for implantation in the cavity; arthroscopically implanting the adjustable tensioning and securing device in the cavity; pulling and holding the free end of the sutures away from the tensioning and securing device in a first direction to tension the sutures; and pulling and holding the free end of the sutures away from the tensioning and securing device in a second direction, and then releasing the sutures to secure the sutures in the tensioning and securing device.

In another embodiment, the present method and apparatus for rotator cuff repair involves a tensioning and securing device for tensioning and securing a rotator cuff tendon to a humeral head. The tensioning and securing device comprises: a body, the body having an outer diameter, a lateral end and a distal end, a mounting section, and a suture opening lateral of the mounting section, the body sized to fit in a cavity created in a lateral section of a humeral head; a face member attached to the lateral end, the face member extending beyond the outer diameter of the body; a first arm, the first arm having a base end and a securing end, the base end pivotally mounted to a first shaft attached to the mounting section; a second arm, the second arm having two side members and a center member, the second arm pivotally mounted at the side members to a second shaft attached to the first arm near the locking end; wherein rotating the second arm towards the lateral end of the body to contact the mounting section draws the securing end of the first arm into engagement with the center member of the second arm to prevent movement of a suture or sutures located therebetween, In another embodiment involving a tensioning and securing device for tensioning and securing a rotator cuff tendon to a humeral head, the tensioning and securing device comprises: a body, the body having an outer diameter, a lateral end and a distal end, body steps, and a suture opening distal of the body steps, the body sized to fit in a cavity created in a lateral section of a humeral head; a face member attached to the lateral end, the face member extending beyond the outer diameter of the body; a tensioning wheel, the tensioning wheel rotatably mounted on a shaft attached to the body; a securing wheel, the securing wheel configured to move along the body steps, the movement of the securing wheel in a proximal direction limited by at least one retention member, the movement of the securing wheel in a distal direction limited by the tensioning wheel and the body steps; wherein the tensioning and securing device is configured to prevent the distal movement of a suture passing through the tensioning and securing device by trapping the suture between the tensioning wheel and the securing wheel, Yet another embodiment of the present method and apparatus for rotator cuff repair involves a surgical burr useful for creating the trough in the humeral head.

A surgical burr for creating a trough in the top of a humeral head may comprise: a handle; a power supply; a power control switch; a depth control switch; a sleeve, the sleeve having a proximal end and a distal end, the sleeve attached to the handle at the proximal end, and the sleeve having an angled bend at the distal end; a burr shaft, the burr shaft having a proximal end and a distal end; the burr shaft housed within the sleeve; a burr, the burr located on the distal end of the burr shaft; wherein the burr is extendable from the sleeve to a depth sufficient to create a trough in the top of a humeral head when the burr is extended from a position adjacent to the top of the humeral head.

Additional objects and advantages of the invention are set forth in, or will be apparent to those of ordinary skill in the art from the detailed description herein. Also, it should be further appreciated that modifications and variations to the specifically illustrated and discussed features or materials hereof may be practiced in various embodiments and uses of this invention without departing from the spirit and scope thereof, by virtue of present reference thereto. Such variations may include, but are not limited to, substitution of equivalent means and features or materials for those shown or discussed, and the functional or positional reversal of various parts, features or the like.

BRIEF DESCRIPTION OF SEVERAL VIEWS OF THE DRAWINGS

A full and enabling disclosure of the present invention, including the best mode thereof, directed to one of ordinary skill in the art, is set forth in the specification, which makes reference to the appended figures, in which.

Figure 1:
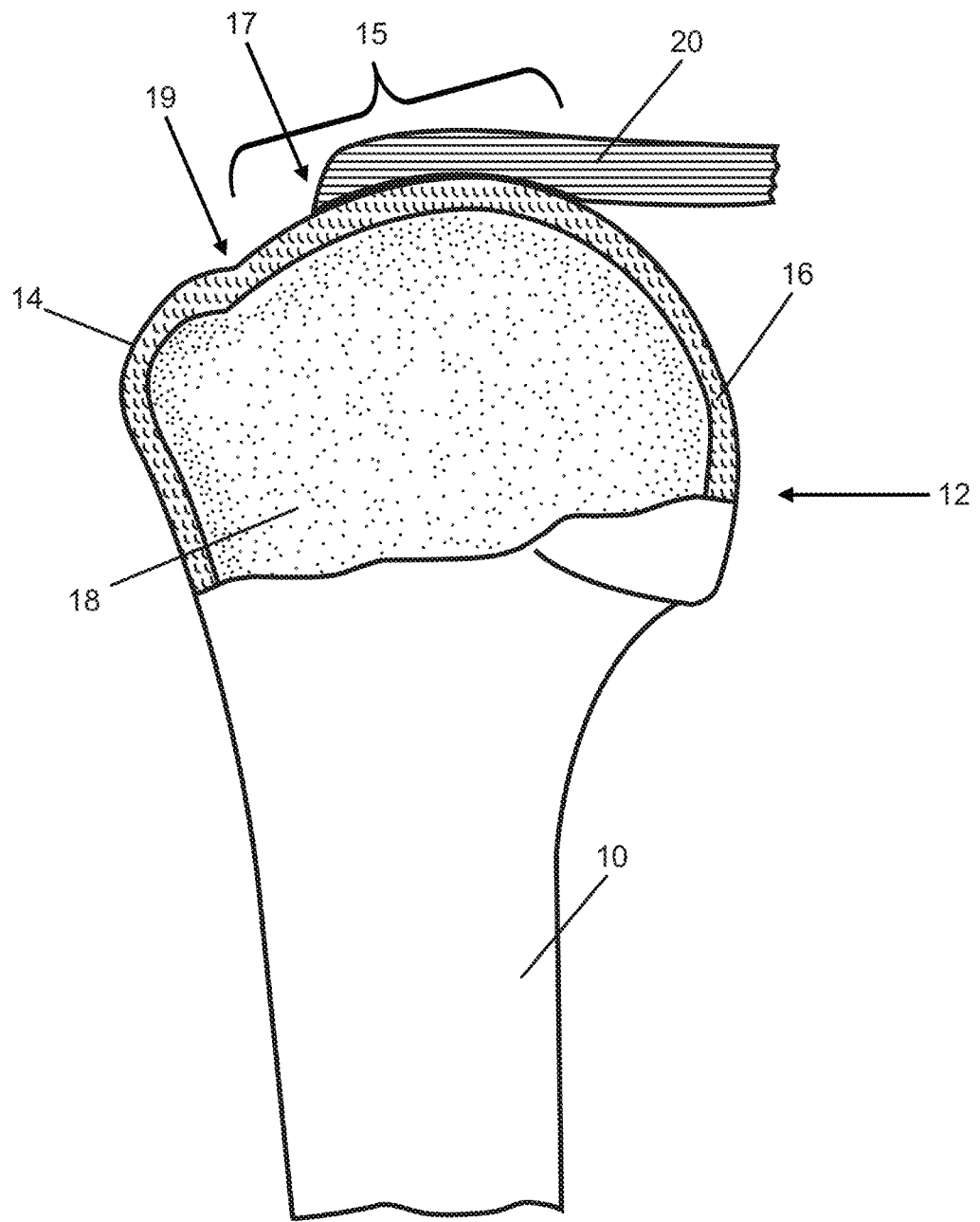
FIG. 1 illustrates a lateral view of the upper portion of a humerus, including the humeral head and a rotator cuff tendon, in partial cross section.

Repeat use of reference characters throughout the present specification and appended drawings is intended to represent same or analogous features or elements of the invention.

DETAILED DESCRIPTION OF THE INVENTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on or with another embodiment to yield a still further embodiment. Thus, it is intended that the present invention cover such modifications and variations. Other objects, features and aspects of the present invention are disclosed in or are apparent from the following detailed description. It is to be understood by one of ordinary skill in the art that the present discussion is a description of exemplary embodiments only, and is not intended as limiting the broader aspects of the present invention.

With respect to rotator cuff repairs, the surgeon has a choice as to patient position, either the beach chair position or, more traditionally for the arthroscopic technique, a lateral decubitus position. Once positioning has been performed, the patient is prepped and draped in the usual sterile fashion, and standard portals are established. A diagnostic arthroscopy is done in the glenohumeral joint first and then attention is directed toward the subacromial space. Access portals (not shown) are made on demand and are usually localized well with a spinal needle. The main access portals for this procedure are lateral portals to access the lateral gutter inferiorly within the recess. These can be visualized through the posterior standard portal and the working portals are generally lateral working portals or anterior portals. It is up to the surgeon's discretion to address the acromio-clavicular (AC) joint or the coraco-acromial (CA) ligament, and to decide whether a subacromial decompression is to be performed. After that is performed, the procedure is started by localizing the lateral access portals.

FIG. 1 depicts the upper portion of a humerus 10 and a torn rotator cuff tendon 20 lying on top of the humeral head 12. The rotator cuff tendon 20 is detached from its footprint 15, and therefore somewhat retracted from its normal, attached position, in which free end 17 would ordinarily extend near area 19. A partial cutaway view of the humeral head shows the surface of the humeral head 14, a layer of cortical bone 16, and the inner cancellous bone marrow 18. When repairing rotator cuff tendons that have torn or detached, it may be necessary to suture a frayed end of the tendon 20 back together, and remove scar tissue and bursa, as well as other material from previous repairs (not shown).

Figure 2:
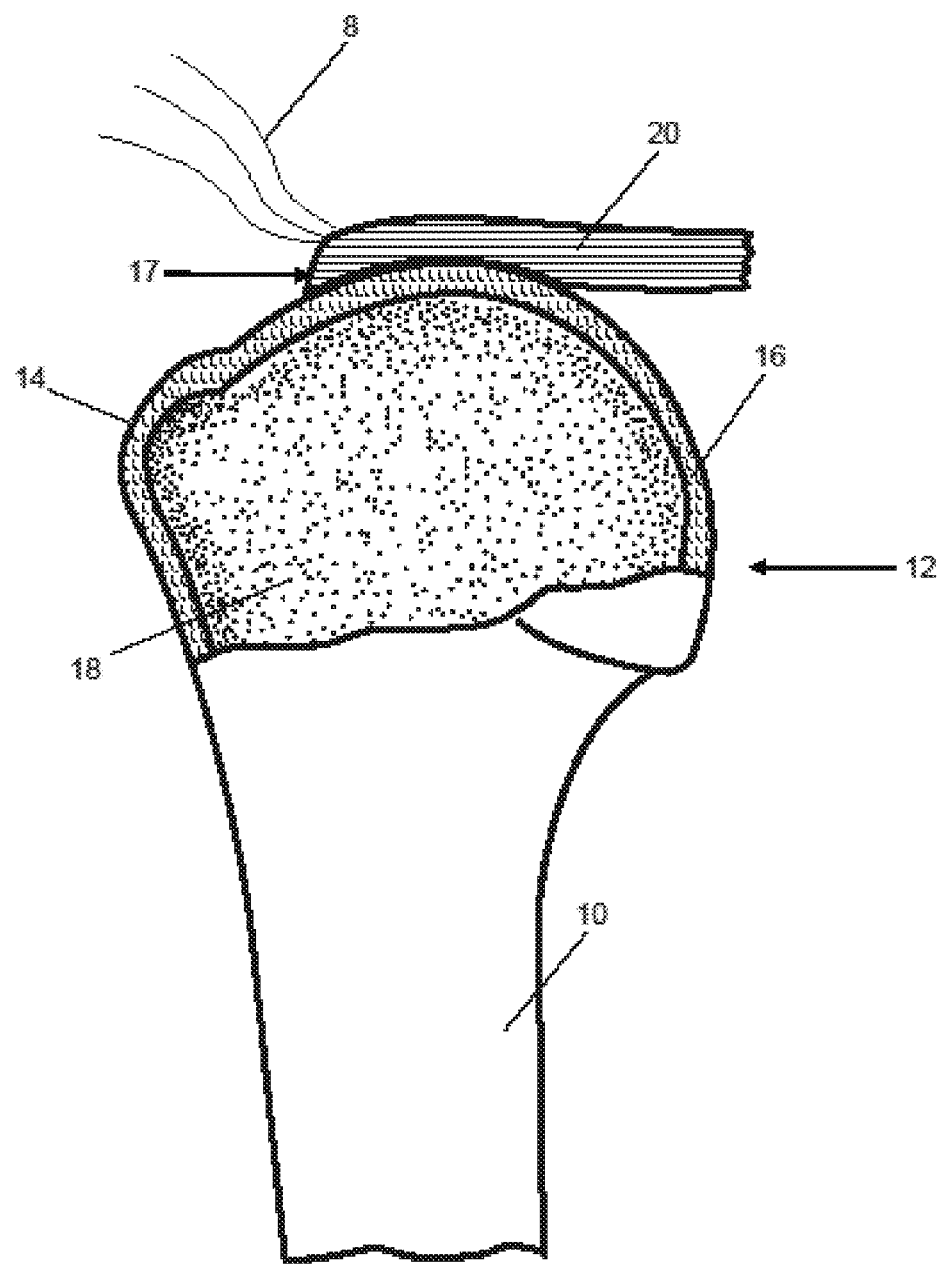
FIG. 2 illustrates sutures attached to the rotator cuff tendon depicted in FIG. 1

Turning now to FIG. 2, in accordance with one embodiment of the present arthroscopic method for rotator cuff repair, sutures 8 are arthroscopically attached to free end 17 of tendon 20. These are preferably horizontal mattress sutures, which may be employed with whatever existing suturing device the surgeon feels most comfortable. Once sutures 8 are placed at the free end 17 of tendon 20, sutures 8 are put aside through another accessory portal (not shown) to keep them out of the way.

Figure 3:
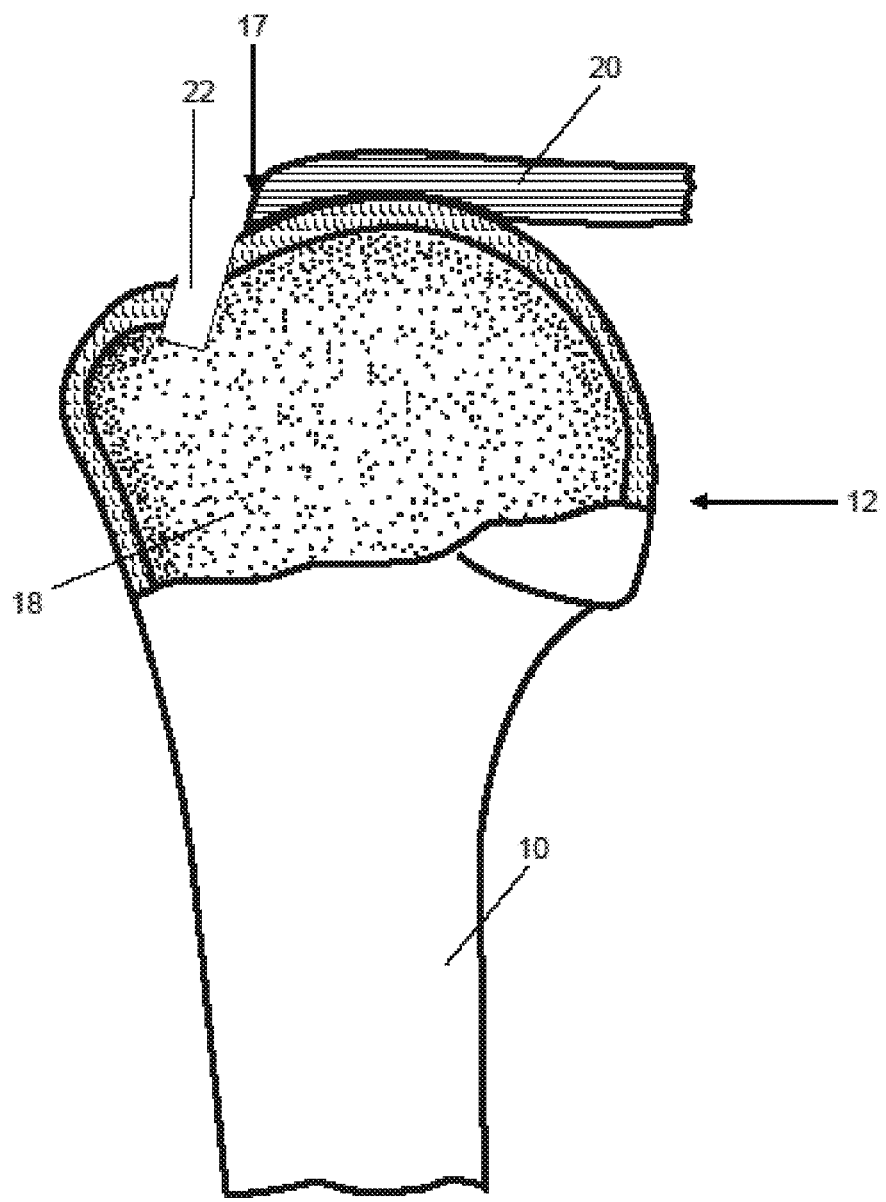
FIG. 3 illustrates a trough created in the humeral head depicted in FIG. 2.

Turning now to FIG. 3, the next step in this embodiment of the present arthroscopic method for rotator cuff repair is to arthroscopically create trough 22 in humeral head 12. Trough 22 is sized to accommodate a portion of the free end 17 of tendon 20. Trough 22 preferably extends at a relatively shallow angle, fifteen degrees for example, into the inner cancellous bone marrow 18. A sharp angle, ninety degrees for example, could present a sharp edge that could damage tendon 20. However, the corner of trough 22 could be rounded if desired.

Figure 4:
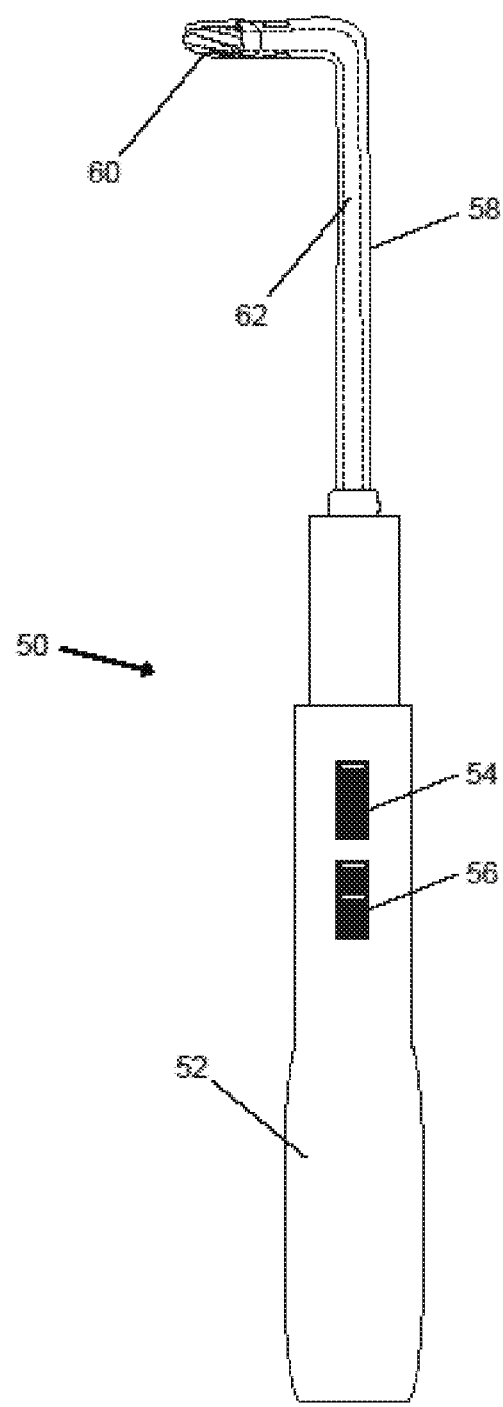
FIG. 4 illustrates a cross-sectional view of a telescoping right-angle burr

Trough 22 is preferably created using a special surgical angle burr 50, which may be similar to that depicted in FIG. 4. Surgical burr 50 may comprise a power supply (not shown), a handle 52, power control 54, depth control 56, sleeve 58, burr section 60, extendable shaft 62. Extendable right angle burr tool 50 also preferably comprises a suction mechanism (not shown) to remove fluid and debris from the burr area during operation. For example, the suction mechanisms may be similar to those employed on existing surgical burr tools. Suction may be controlled by operation of power control 54, or by a separate control (not shown). Fluid and debris from the burr area during operation may be facilitated by a suction tube (not shown), or by sleeve 58. Fluid and debris will travel through the tube or sleeve 58 when suction is activated during operation of surgical burr 50. Surgical burr 50 may be constructed from a variety of suitable medical-grade materials as desired and/or required by law.

Burr section 60 may be extended, for example, using an extendable shaft 62 that extends into sleeve 58, where extendable shaft 62 is rigid enough to provide pressure on burr section 60 to create trough 22, but flexible enough to pass through the angled section 64 of sleeve 58 as extendable shaft 62 extends burr section 60. Burr section 60 could also be extended, for example, using an extendable shaft 62 having telescoping sections (not shown) near burr section 60 that telescope burr section 60.

Power control 54 may be an on-off switch, a variable speed switch or dial, or other type of steady or variable power sliding switch known to those of skill in the art. Similarly, depth control 56 may be an on-off switch or dial, wherein turning the switch on when burr section 60 is in position on the humeral head would create a trough of a pre-set depth. Depth control 56 may include a multiple position switch that would allow for multiple pre-set depth levels that the surgeon can choose from. The power source may be an electrical or pneumatic source, or other power source available in the operating room and suitable for operating a surgical instrument, such as surgical burr 50.

Depth control 56 may also be a variable depth sliding switch or dial, wherein right angle burr tool 50 may further comprise a depth indicator. Again, depth control 56 may employ various types of switches that can activate single or variable depth operation, as known to those of skill in the art.

While it is preferable to use a right angle burr tool 50 to create the trough 22, trough 22 may be formed by identifying the rotator cuff footprint and then using a conventional arthroscopic burr to create a trough. If the depth needs to be increased, then angled curretes can be used to deepen the trough with arthroscopic visualization.

In this embodiment of the present arthroscopic method for rotator repair, surgical burr 50 is used through the anterior working portal while the arthroscope positioned in the posterior portal for superior visualization of trough 22 as it is created. Thus, the burr will not obstruct the view of the procedure. The exact position of trough 22 is approximate, not fixed, to give the surgeon flexibility once the actual physical situation is assessed arthroscopically. For example, the surgeon can medialize trough 22 in humeral head 12 if a retracted tear is encountered that does not have a great deal of movement. On the other hand, if the tear is not so retracted and/or has greater movement, the surgeon may place trough 22 in the more anatomic position shown in FIG. 3.

Figure 5:
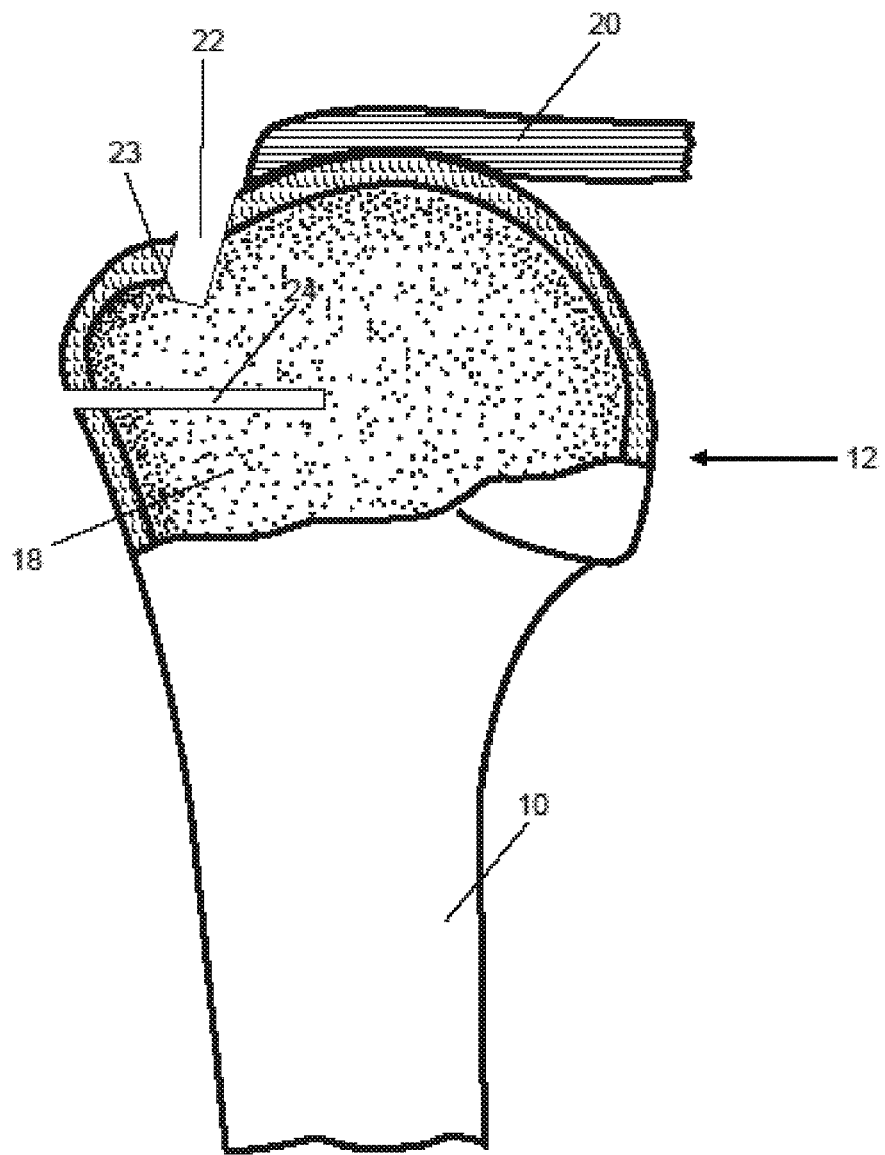
FIG. 5 illustrates a pilot hole drilled in the humeral head depicted in FIG. 3.
Figure 6:
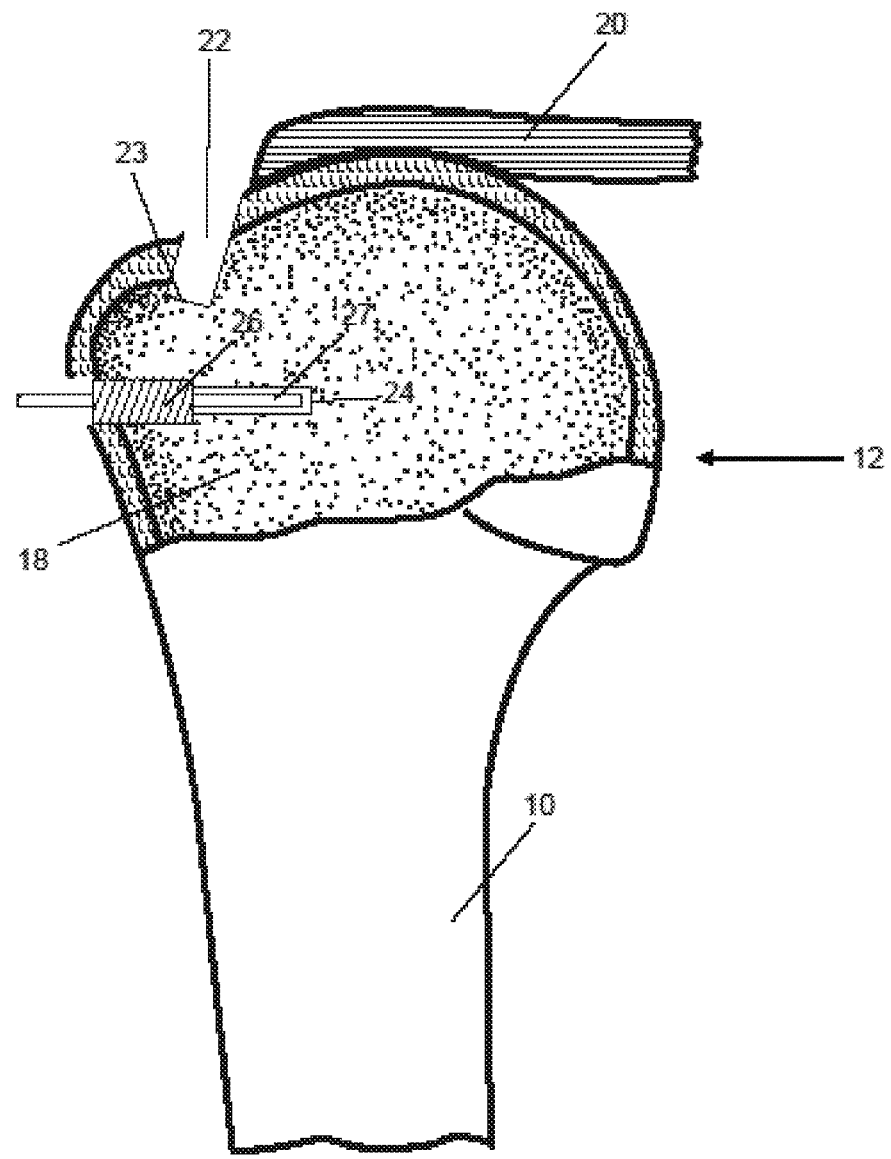
FIG. 6 illustrates a burr reaming the pilot hole created in the humeral head depicted in FIG. 5.

As seen in FIG. 6, a guide pin 27 is poised to arthroscopically create a pilot hole 24 (see FIG. 5) in the lateral cortex. The guide pin 27 is introduced through the lateral working portal. The location for pilot hole 24 may be determined by positioning the guide pin 27 on the flair of the lateral cortex. A guide (not shown) may also be used, but is not required. The pilot hole 24 is placed on the flair of the lateral cortex such that it is not too low on the lateral margin for creation of the tunnel(s) 32 (see FIG. 8), or too close to trough 22 such that the humeral head becomes unacceptably weakened, and thus presenting a risk of fracture. Pilot hole 24 preferably extends into the inner cancellous bone marrow 18 to a point beyond the lateral edge 23 of trough 22. A depth stop or visual indicator on the guide pin 27 may be used to achieve the desired depth (not shown).

In accordance with this preferred embodiment of the present arthroscopic method of rotator cuff repair, and as seen in FIG. 6, the surgeon then introduces a cannulated reamer 26 over the guide bit 27 (used to create the pilot hole) and through the lateral working portal to ream the lateral cortex and enlarge pilot hole 24. Guide pin 27 extends into the pilot hole 24 and serves to guide reamer 26 as it creates cavity 28.

Cavity 28 preferably extends into the inner cancellous bone marrow 18 to a point near or slightly lateral of the lateral edge 23 of trough 22. A depth stop or visual indicator on the reamer may be used to achieve the desired depth. During drilling and reaming, the arthroscope (not shown), may be positioned posterior to the operation so that direct visualization of cavity 28 will be noted.

Figure 7:
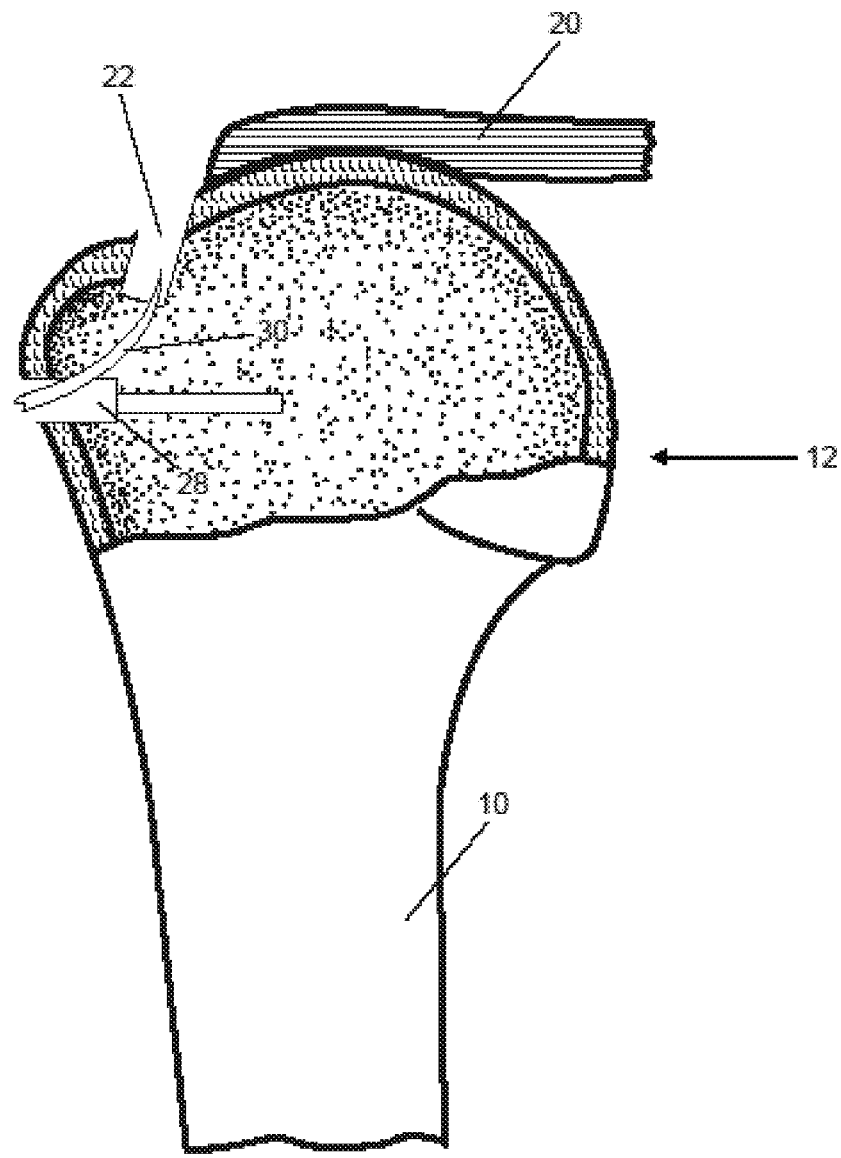
FIG. 7 illustrates an awl creating a tunnel between the reamed cavity and the trough in the humeral head depicted in FIG. 6.

Once cavity 28 has been formed, an awl 30 is introduced through the lateral working portal and cavity 28, and pushed through the inner cancellous bone marrow 18 and into trough 22 as seen in FIG. 7. Awl 30 has a built-in radius of curvature that will ensure that awl 30 emerges in trough 22. Awl 30 is then withdrawn from humeral head 12 and the lateral working portal, which creates tunnel 32 (see FIG. 8). Multiple tunnels may be created using multiple awls.

Figure 8:
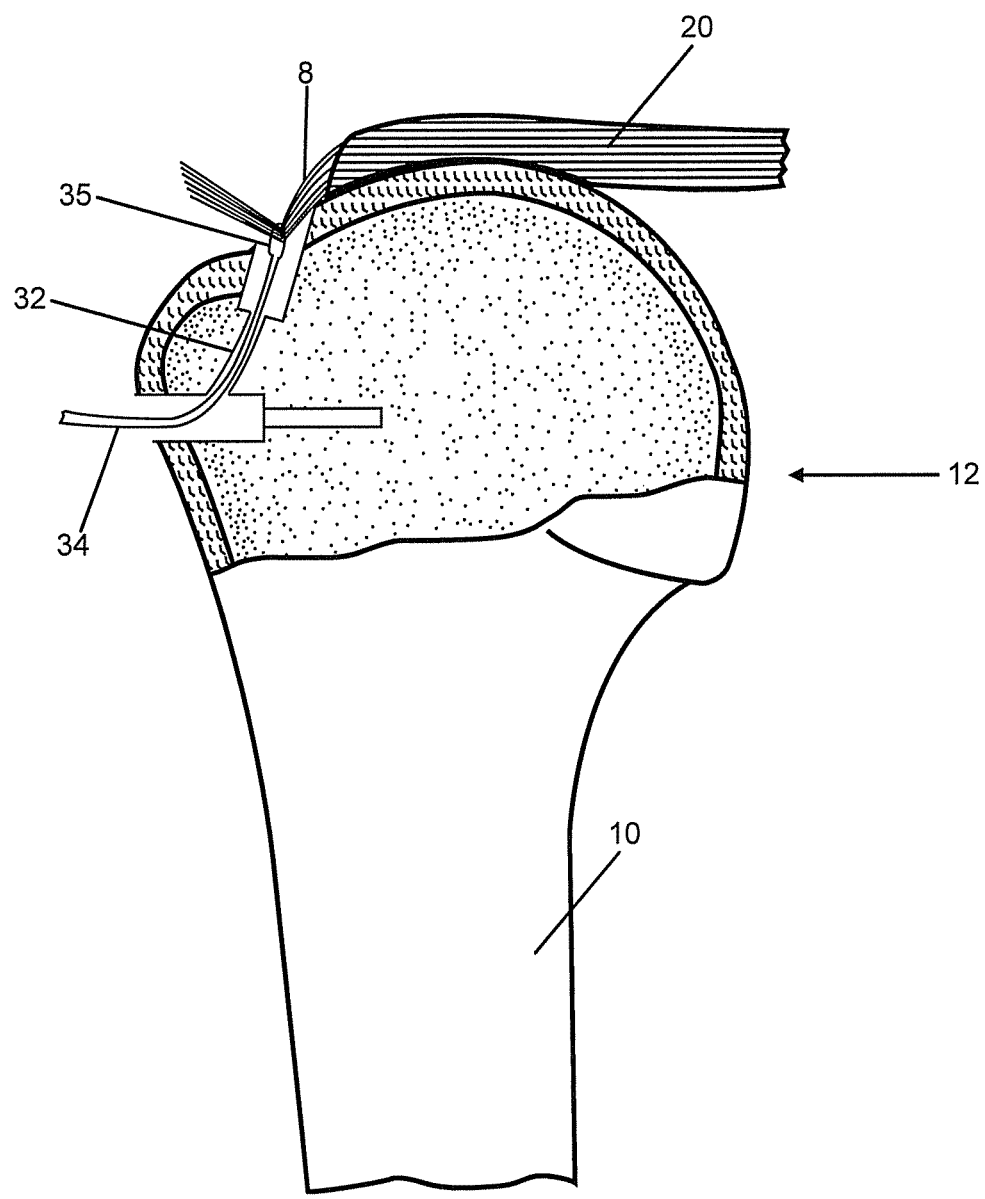
FIG. 8 illustrates a suture retriever passed through the tunnel in the humeral head depicted in FIG. 7.
Figure 9:
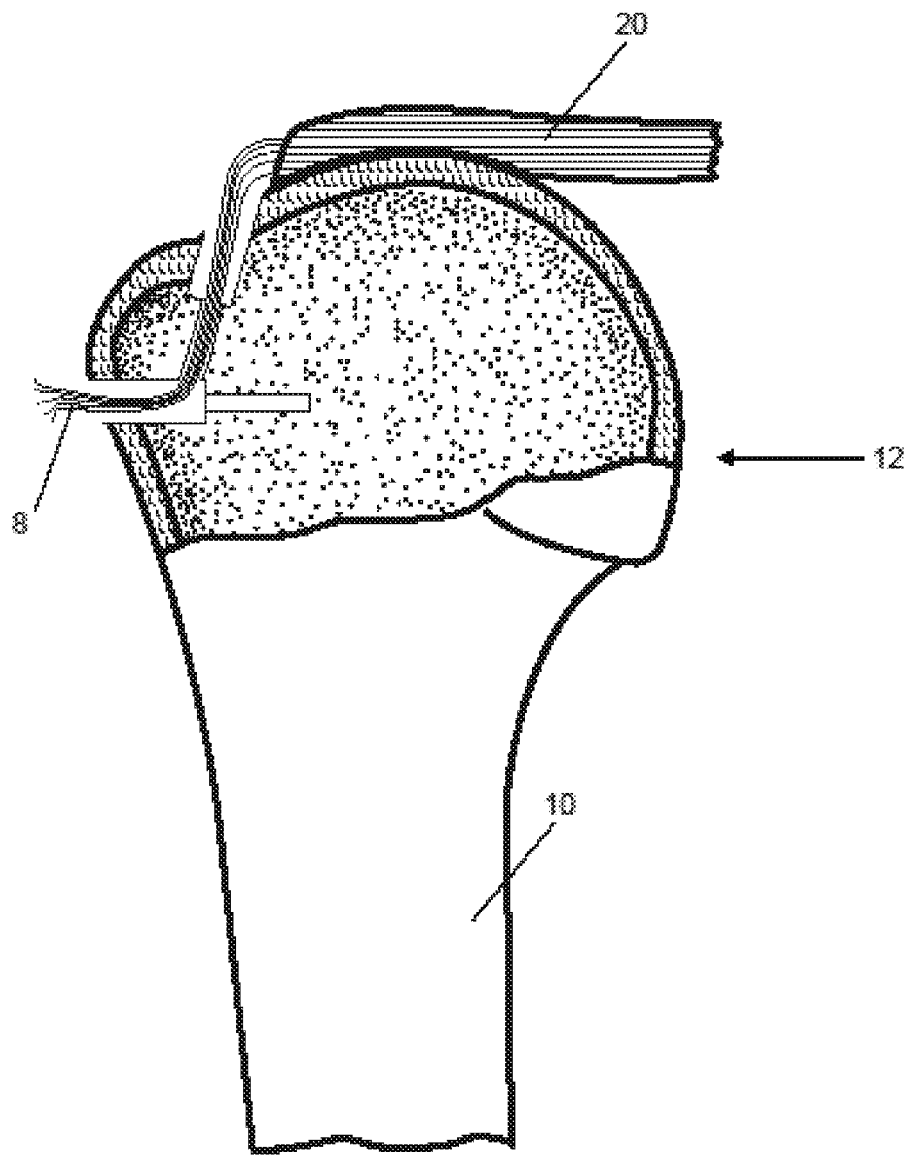
FIG. 9 illustrates sutures retrieved through the tunnel in the humeral head depicted in FIG. 8.

Once tunnel 32 has been created, a suture retriever 34 is introduced through the lateral working portal and into cavity 28, and then pushed through tunnel 32 and into trough 22 as seen in FIG. 8. Sutures 8 are then removed from the accessory portal and routed through loop 35 on suture retriever 34. Suture retriever 34 and sutures 8 are then pulled back through tunnel 32 and cavity 28 as seen in FIG. 9. Suture retriever 34 and sutures 8 are then removed from the lateral access portal.

Figure 10:
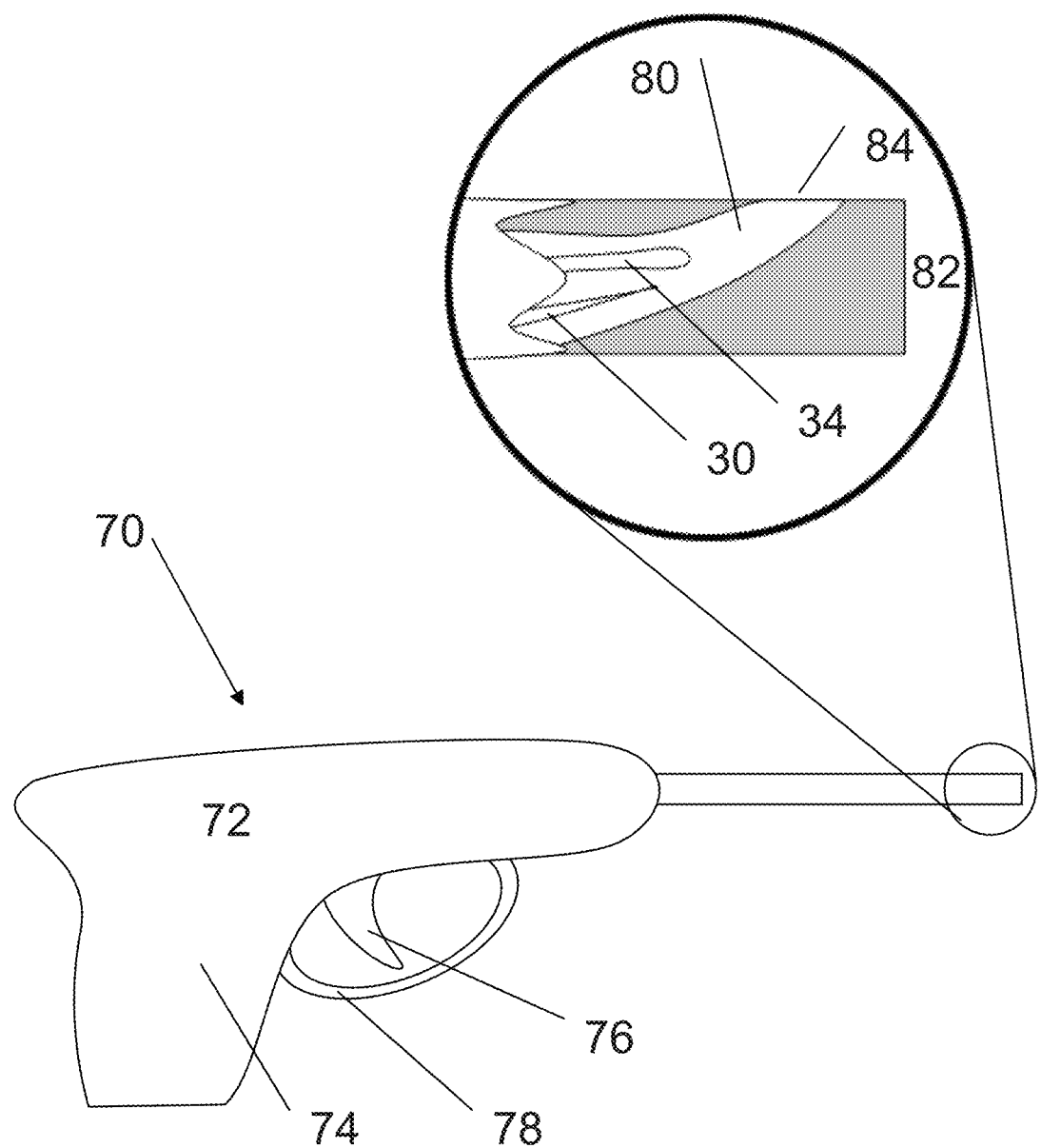
FIG. 10 illustrates a combined awl and suture retriever deployment device, including an end portion in partial cross-section.

Turning now to FIG. 10, it may be preferable to introduce suture retriever 34 and awl 30 to cavity 28 using a deployment device 70 to guide awl 30 and suture retriever 34 into tunnel 32. The device 70 may deploy only one or multiple suture retrievers 34 and/or awls 30. As depicted in FIG. 10, the device 70 is a combined awl and suture retriever that can deploy awl 30, and then suture retriever 34 without the surgeon having to use separate devices. Such deployment devices 70 incorporate a depth stop formed either by configuring the length from the proximal end 82 of device 70 to the opening 84 or providing, for example, an external collar, tab or the like (not shown) to ensure that suture retriever 34 and/or awl 30 line-up with tunnel 32 when deployed.

As depicted in FIG. 10, deployment device 70 includes a body 72, which includes handle 74, an awl 30, and a suture retriever 34. Deployment may be performed manually, using for example trigger 76, a lever or the like (not shown), or automatically using for example, trigger 76, a switch or button or the like and an electric motor and gears (not shown). Trigger guard 78 may be used to prevent accidental deployment of awl 30 and/or suture retriever 34. Awl 30 and suture retriever 34 may be guided to opening 84 by deployment guide 80. Multiple triggers 76 or a single trigger and a selector switch 75, or a selector lever, levers, switches, etc. (not shown) may be employed to activate individual awls 30 and/or suture retrievers 34. For example, positioning switch 75 to position A may configure the trigger 76 mechanism to operate an awl 30 while positioning switch 75 to position B configures the trigger 76 mechanism to operate suture retriever 34.

The combined awl and suture retriever 70 may serve to simplify and speed up the ordinarily complex arthroscopic procedure. For instance, rather than insert an awl 30 by hand to form a tunnel 32, and then hand guide a suture retriever 34 through the tunnel 32, the surgeon may simply insert the combined awl and suture retriever 70 into cavity 28 and activate the awl 30 by, for example, pressing and releasing a trigger 76 to create a tunnel 32, and then, for example, pressing a second trigger 76 to deploy suture retriever 34, threading sutures 8 through suture retriever 34, and then releasing second trigger 76 and removing combined awl and suture retriever 70 from cavity 28 and the lateral access portal (not shown).

Figure 11:
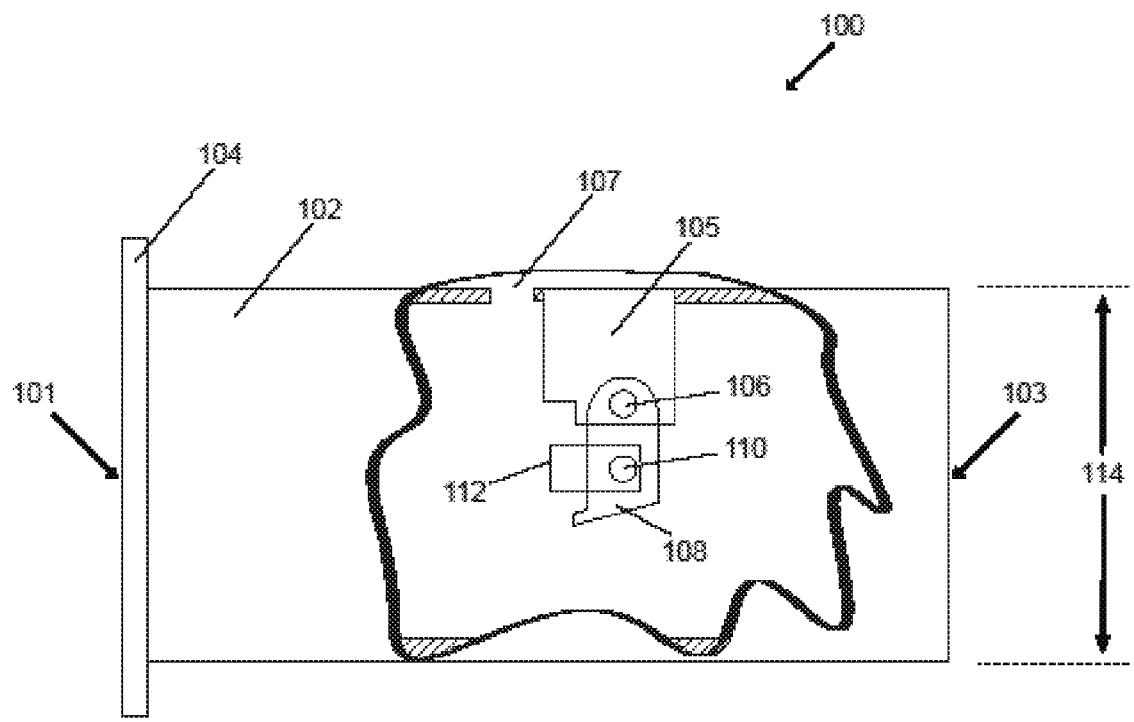
FIG. 11 illustrates a partially cutaway side view of a preferred embodiment of the present combination suture tensioning and securing device.
Figure 12:
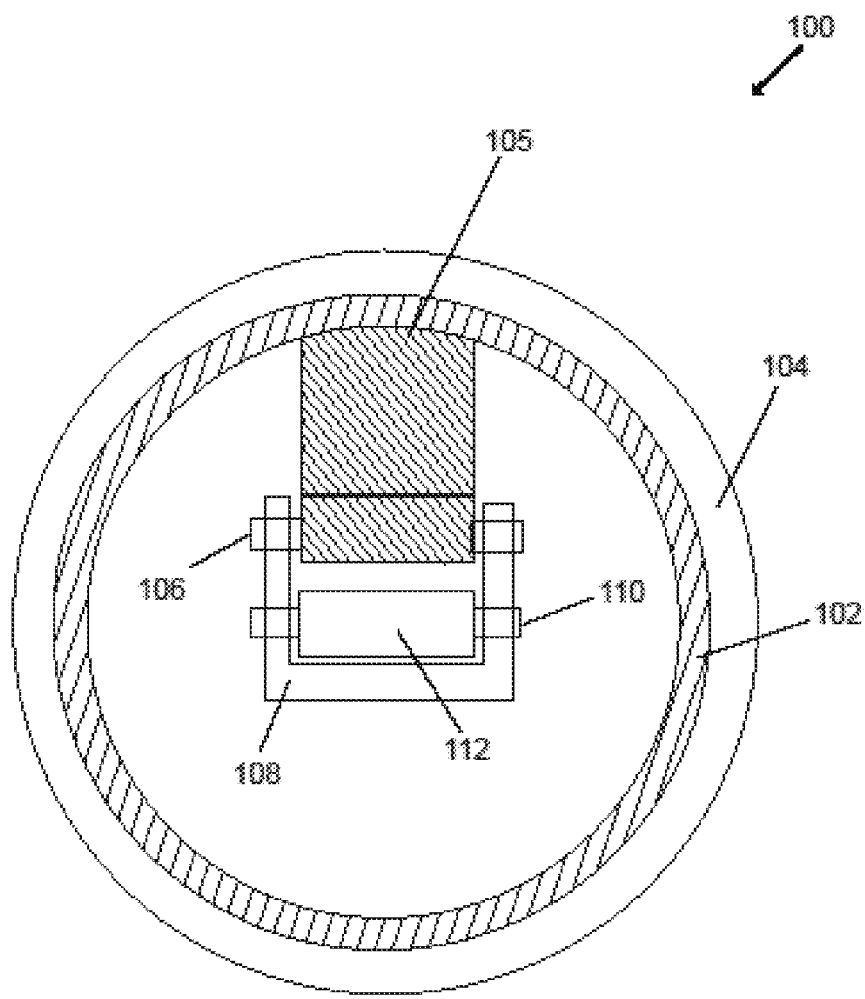
FIG. 12 illustrates a proximal end view of the combination suture tensioning and securing device of FIG. 11.
Figure 13:
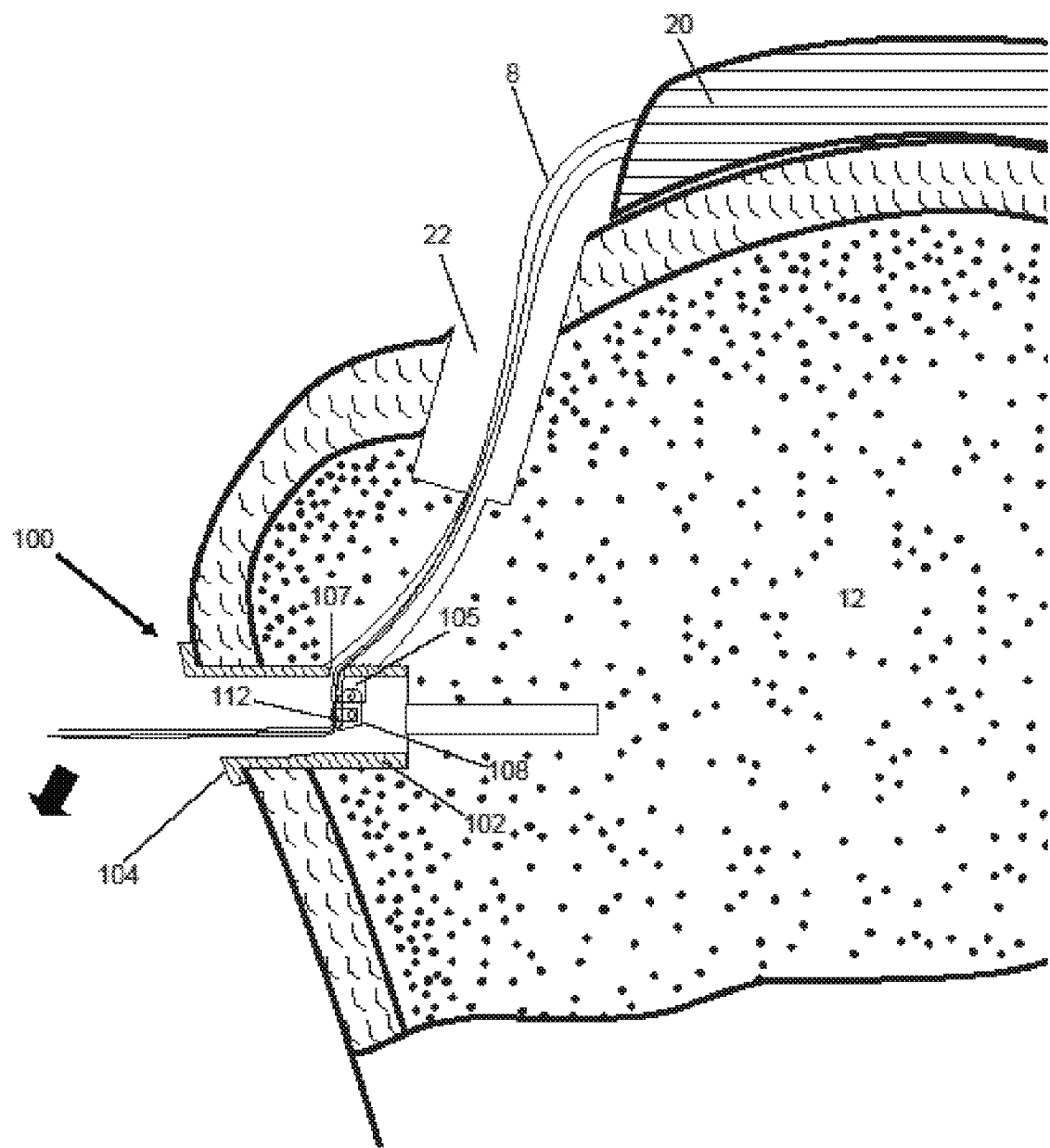
FIG. 13 illustrates the combination suture tensioning and securing device positioned in the humeral head depicted in FIG. 9.

Once suture retriever 34 and sutures 8 are removed from the lateral access portal, sutures 8 are inserted through a tensioning and securing device 100 (see, e.g., FIGS. 12 and 13). Tensioning and securing device is then implanted into cavity 28, and tendon 20 is positioned in trough 22 and sutures 8 are tensioned and secured. Alternatively, tendon 20 may be pulled manually into trough 22 using sutures 8 before inserting sutures 8 through the tension and securing device. The structure and operation of tensioning and securing device is illustrated in FIGS. 11-12.

As its name implies, tensioning and securing device 100 tensions and secure the rotator cuff tendon 20 in trough 22. It protects the bone from any sawing action of the sutures 8 through the lateral cortex. Moreover, it functions to distribute the force applied to the surface of the lateral cortex.

FIG. 11 depicts a cutaway side view of tensioning and securing device 100 in accordance with a preferred embodiment of the present arthroscopic method of rotator cuff repair. Tensioning and securing device 100 comprises circular body 102, face member 104, first shaft 106, first arm 108, second shaft 110, and second arm 112. Tensioning and securing device 100 is shown in an unsecured or tensioning position.

Body 102 further comprises a suture opening 107 and a mounting section 105. Body 102 has an outer diameter 114, a proximal end 101, and a distal end 103. Outer diameter 114 of body 102 is sized to fit within cavity 28, with face member 104 abutting the lateral surface of humeral head 12 (see FIG. 14). Body 102 may be made from a relatively strong material that is also compatible for use in a medical implant, such as medical grade stainless steel. Other parts of tensioning and securing device 100 may also be made from similar materials. It should be understood that, while body 102 is preferably circular in cross-section (see, e.g., FIGS. 12 and 13), other cross-sectional body shapes that are sized to fit within cavity 28 are also envisioned, including, but not limited to, triangular, square, hexagonal, octagonal, etc.

Face member 104 extends beyond the outer diameter 114 of body 102, and thus serves to limit the depth of insertion of tensioning and securing device 100 in cavity 28. Further, face member 104 prevents movement of tensioning and securing device 100 as tendon 20 is tensioned in trough 22 (see, e.g., FIG. 15). It should be understood that, while face member 104 is depicted as flange-like, other configurations of face member that limit the depth and movement of tensioning and securing device 100 in cavity 28 are also within the scope of the present tensioning and securing device 100. For example, face member 104 could be comprised of an arm or arms extending from a portion of the circumference of the body 102 (not shown) rather than a flange-like face member extending from the entire circumference of the body 102. However, a face member that distributes over a relatively large area the lateral force on humeral head 12 resulting from tensioning tendon 20 in trough 22 is preferred, such as flange-like face member 104.

Figure 14:
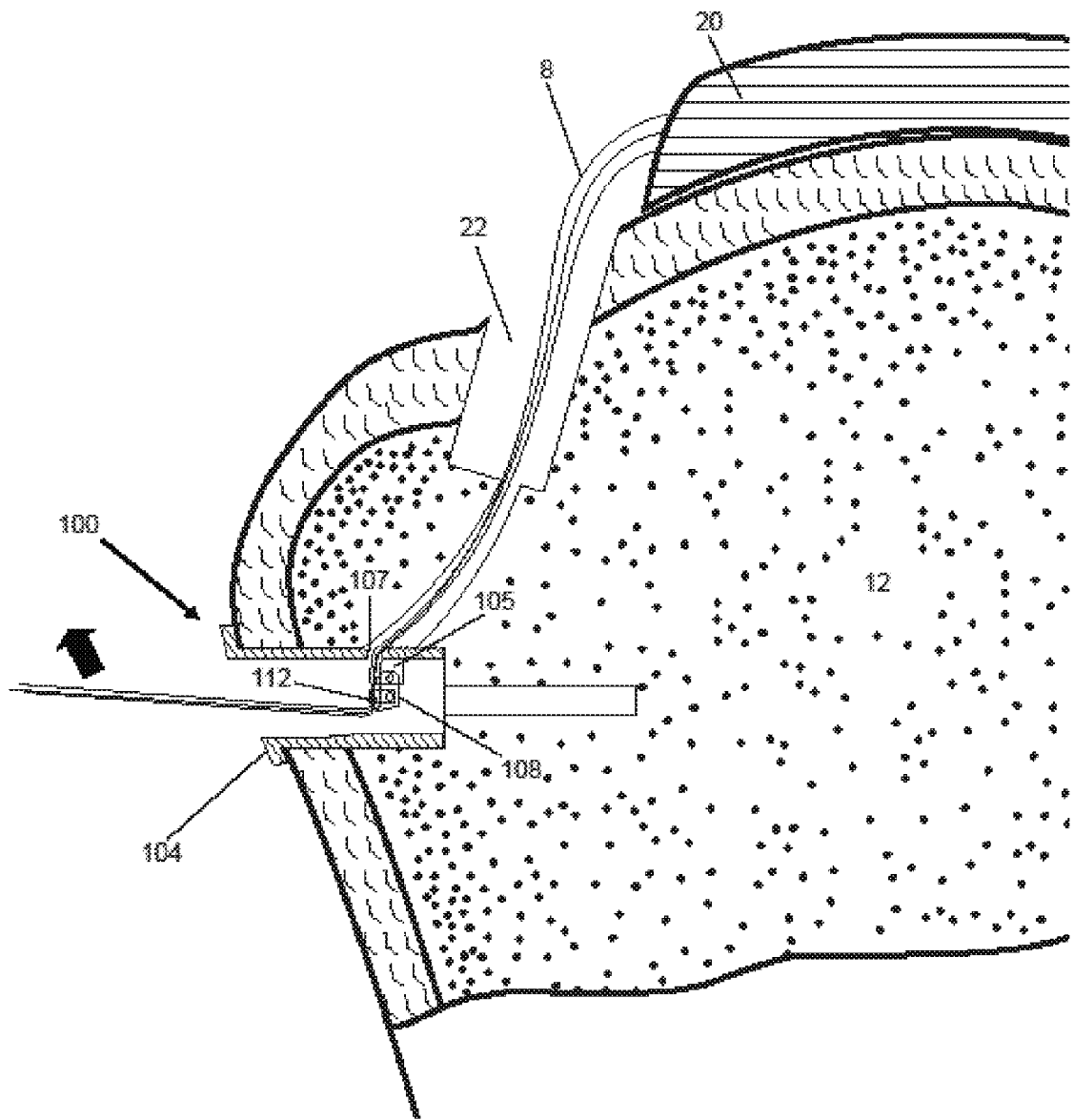
FIG. 14 illustrates the rotator cuff tendon drawn into the trough in the humeral head depicted in FIG. 13.
Figure 15:
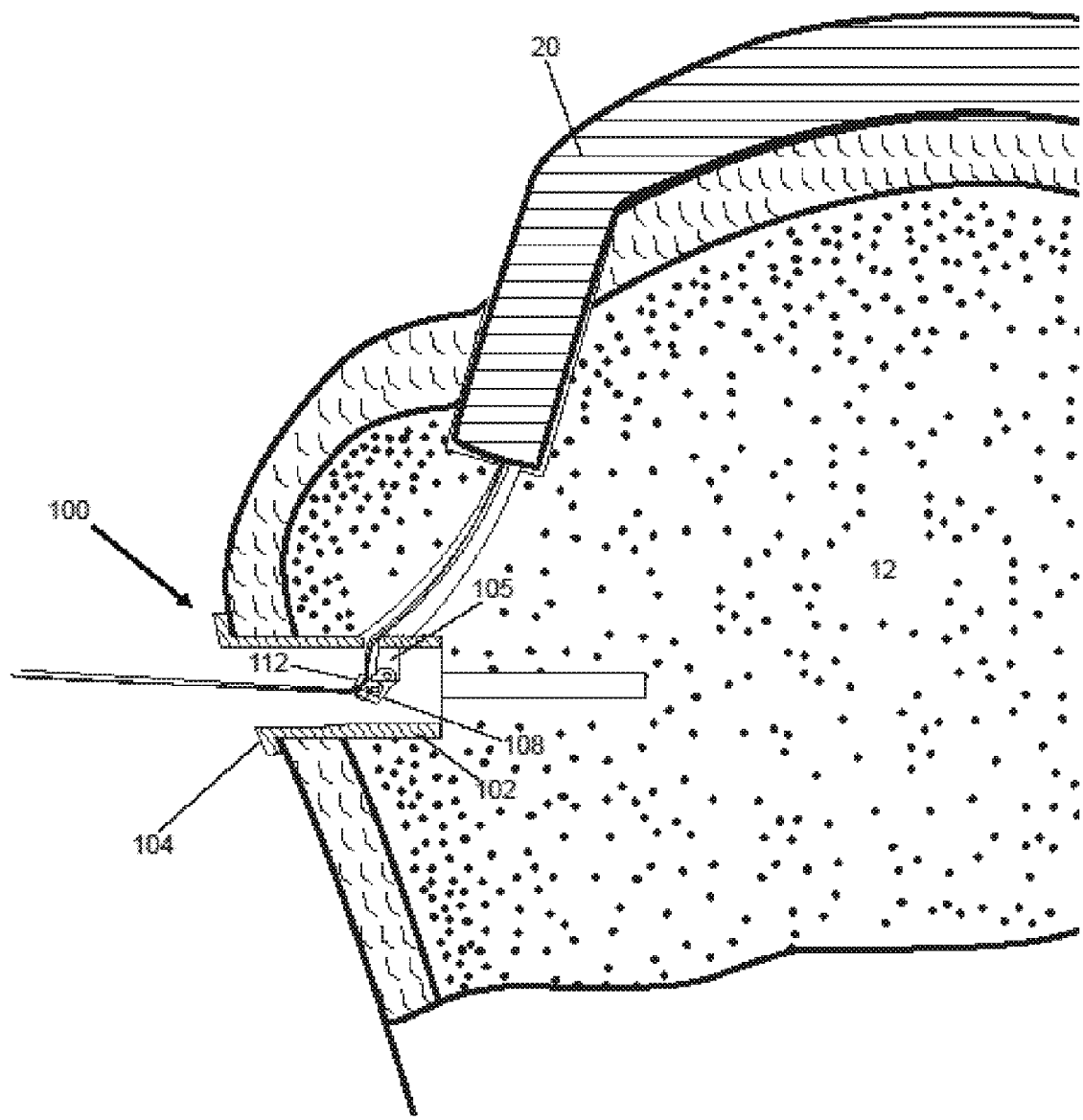
FIG. 15 illustrates the rotator cuff tendon in a secured position in the humeral head depicted in FIG. 14.

FIG. 12 shows tensioning and securing device 100 looking into the device from proximal end 101. First arm 108 is pivotally attached to first shaft 106, which is in turn attached to mounting section 105. Second arm 112 is pivotally attached to second shaft 110, which is in turn attached to first arm 108. In this embodiment, body 102 has a mostly circular inner wall configuration 109. However, inner wall configuration 109 may be one of a variety of configurations that will accommodate the tensioning and securing mechanism, including non-circular configurations. The operation of tensioning and securing device 100 is illustrated in FIGS. 13-15.

Turning now to FIG. 13, tensioning and securing device 100 has been arthroscopic ally inserted into cavity 28 such that face member 104 abuts the lateral surface of humeral head 12. The free ends of sutures 8 were threaded through suture opening 107 lateral of mounting section 105, and then through second arm 112 and out the lateral end 101 of body 102 while sutures 8 and tensioning and securing device 100 were outside of the body, Once tensioning and securing device 100 is in place in the humeral head, sutures 8 are pulled in a direction lateral and downwards in relation to the humeral head, i.e. in the direction of the arrow. Pulling sutures 8 in this direction releases arms 108 and 112 (if tensioning and securing device 100 is in a secured position) or does not engage second arm 112. The surgeon may then continue to pull sutures 8 in the direction of the arrow to draw tendon 20 into trough 22. As mentioned previously, however, tendon 20 may be pre-positioned in trough 22 by pulling on sutures 8 before tensioning and securing device 100 has been inserted into cavity 28.

Once tendon 20 is in trough 22, the surgeon may continue to pull sutures 8 in the direction lateral and downwards in relation to the humeral head, i.e. in the direction of the arrow in FIG. 13. This will apply the desired final amount of tension to sutures 8. The surgeon then pulls sutures 8 in a lateral and upwards direction as depicted in FIG. 15.

Pulling sutures 8 in this direction engages arm 112 and draws second arm 112 into contact with mounting section 105. At the same time, the pivotal connection between first arm 108 and second arm 112 draws first arm 108 over second arm 112, and traps sutures 8 between first arm 108 and second arm 112.

FIG. 15 shows tensioning and securing device 100 in this secured position. Tendon 20 will thus be held in place in trough 22 until biological healing between bone and tendon occurs. Excess suture material may be cut or trimmed back inside tensioning and securing device 100. A cap 114 (see FIGS. 21-23) may be arthroscopically affixed over the lateral opening of tensioning and securing device 100 before closing the surgical portals. This cap 114 may be affixed in a variety of ways, including use of a threaded cap that engages threads in the lateral opening of body 102 (not shown), an interference fit, such as a snap fit, inside the lateral opening of body 102, cementing the cap 114 in place, etc.

Alternatively, cap 114 may be affixed over the lateral opening of tensioning and securing device 100 during manufacture or before tensioning and securing device is arthroscopically inserted into the patient. The cap 114 may also form a second securing point for sutures 8, employing any number of known methods of securing sutures or similar materials. For example, sutures 8 may be pulled under a prong on the cap 114 (not shown), or simply trapped between the cap 114 and body 102 if the cap 114 is snap fit or cemented in place (see FIG. 21), or threaded through a slit 116 in the cap 114 and secured by positioning the sutures 8 in a narrow portion of the slit 116 (see FIG. 22). The face of the cap may be comprised of a flexible material, including, but not limited to, surgical grade rubber for example. The flexibility of the face of cap 114 allows for movement of the sutures 8 to operate tensioning and securing device 100, for instance, while maintaining the lateral opening of tensioning and securing device 100 effectively closed off.

Figure 16:
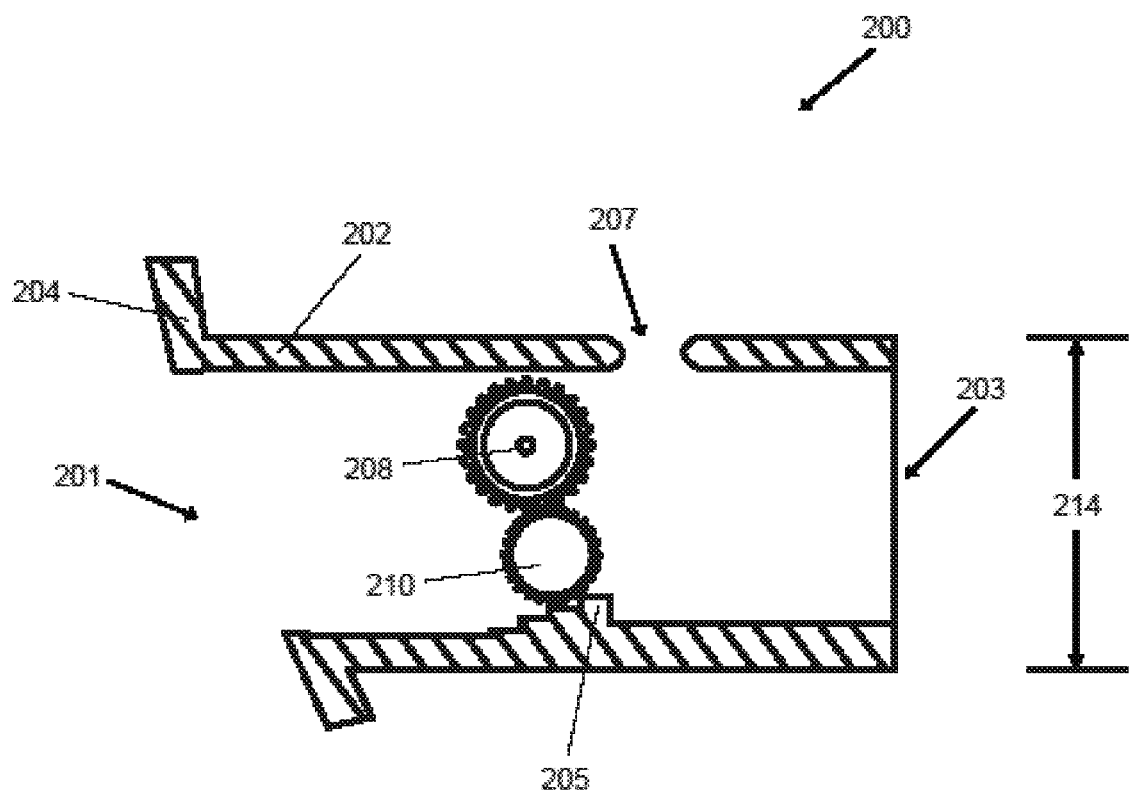
FIG. 16 illustrates a partially cutaway side view of an embodiment of the present combination suture tensioning and securing device.

FIG. 16 depicts an alternate tensioning and securing device 200 in accordance with the present arthroscopic method of rotator cuff repair. Tensioning and securing device 200 comprises a body 202, face member 204, tensioning wheel 206, shaft 208, securing wheel 210, and retention bars 212.

Body 202 has a proximal end 201 and a distal end 203. Body 202 has an outer diameter 214 sized to fit within cavity 28, with face member 204 abutting the lateral surface of humeral head 12 (see FIG. 18). Body 202 may be made from a strong material that is also compatible for use in a medical implant, such as medical grade stainless steel. Other parts of tensioning and securing device 200 may also be made from stainless steel. Body 202 further comprises a suture opening 207 and body steps 205. It should be understood that, while body 202 is preferably circular in cross-section (see, e.g., FIGS. 17 and 18), other cross-sectional body shapes that are sized to fit closely within cavity 28 are also envisioned, including, but not limited to, triangular, square, hexagonal, octagonal, etc.

Face member 204 extends beyond the outer diameter 214 of body 202 and serves to limit the depth of insertion of tensioning and securing device 200 in cavity 28. Further, face member 204 prevents movement of tensioning and securing device 200 as tendon 20 is tensioned in trough 22 (see, e.g., FIGS. 20 and 21). It should be understood that, while face member 204 is depicted as flange-like, other configurations of face member that limit the depth and movement of tensioning and securing device 200 in cavity 28 are also within the scope of the present tensioning and securing device 200. For example, face member 204 could be comprised of an arm or arms extending from a portion of the circumference of the body 202 (not shown) rather than a flange-like face member extending from the entire circumference of the body 202. However, a face member that distributes over a large area the lateral force on humeral head 12 resulting from tensioning tendon 20 in trough 22 is preferred, such as flange-like face member 204.

Tensioning wheel 206 is rotatably mounted on shaft 208. Securing wheel 210 is not mounted to a shaft, but is prevented from excess lateral movement in one direction by retention bars 212 (see FIG. 17), and movement in the opposite direction by contact with the body steps 205 and tensioning wheel 206. Tensioning wheel 206 and securing wheel 210 are preferably rough or toothed to facilitate friction between sutures 8 and wheels 206 and 210.

Figure 17:
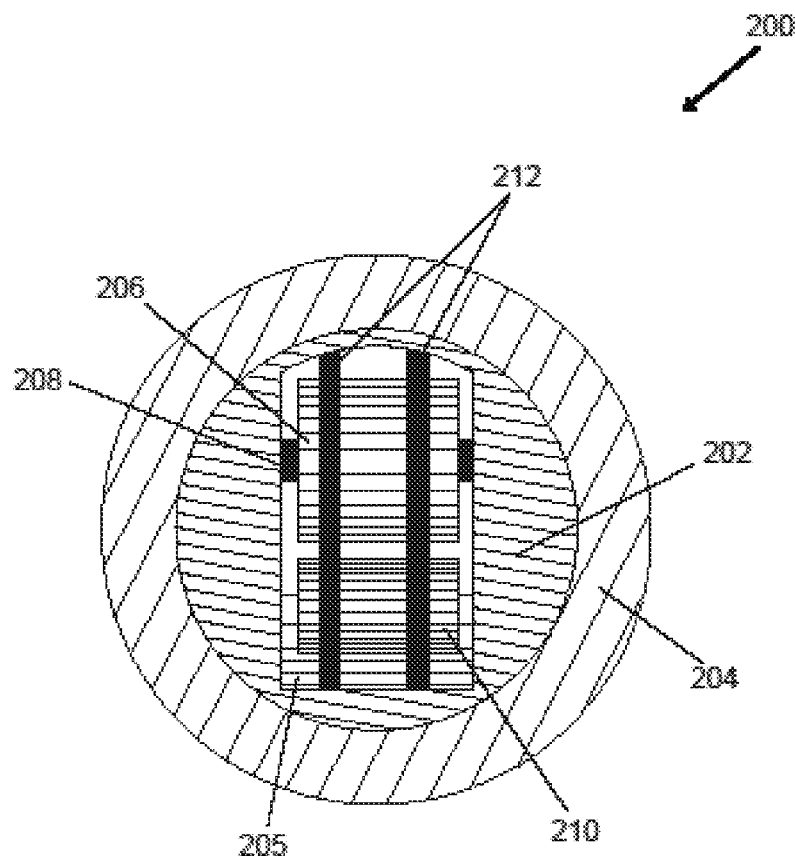
FIG. 17 illustrates a proximal end view of the combination suture tensioning and securing device of FIG. 16.

FIG. 17 shows tensioning and securing device 200 looking into the device from proximal end 201. Here, two retention bars 212 are shown. Retention bars 212 may serve to separate multiple sutures 8 routed through tensioning and securing device 200. Securing wheel 210 is shown in a secured position near the top of body steps 205 to trap suture 8 (not shown) between tensioning wheel 206 and securing wheel 210. In this embodiment, circular body 202 has a non-circular inner wall configuration 209. However, inner wall configuration 209 may be one of a variety of configurations that will accommodate the tensioning and securing mechanism, including a circular configuration. The operation of tensioning and securing device 200 is illustrated in FIGS. 18-20.

Figure 18:
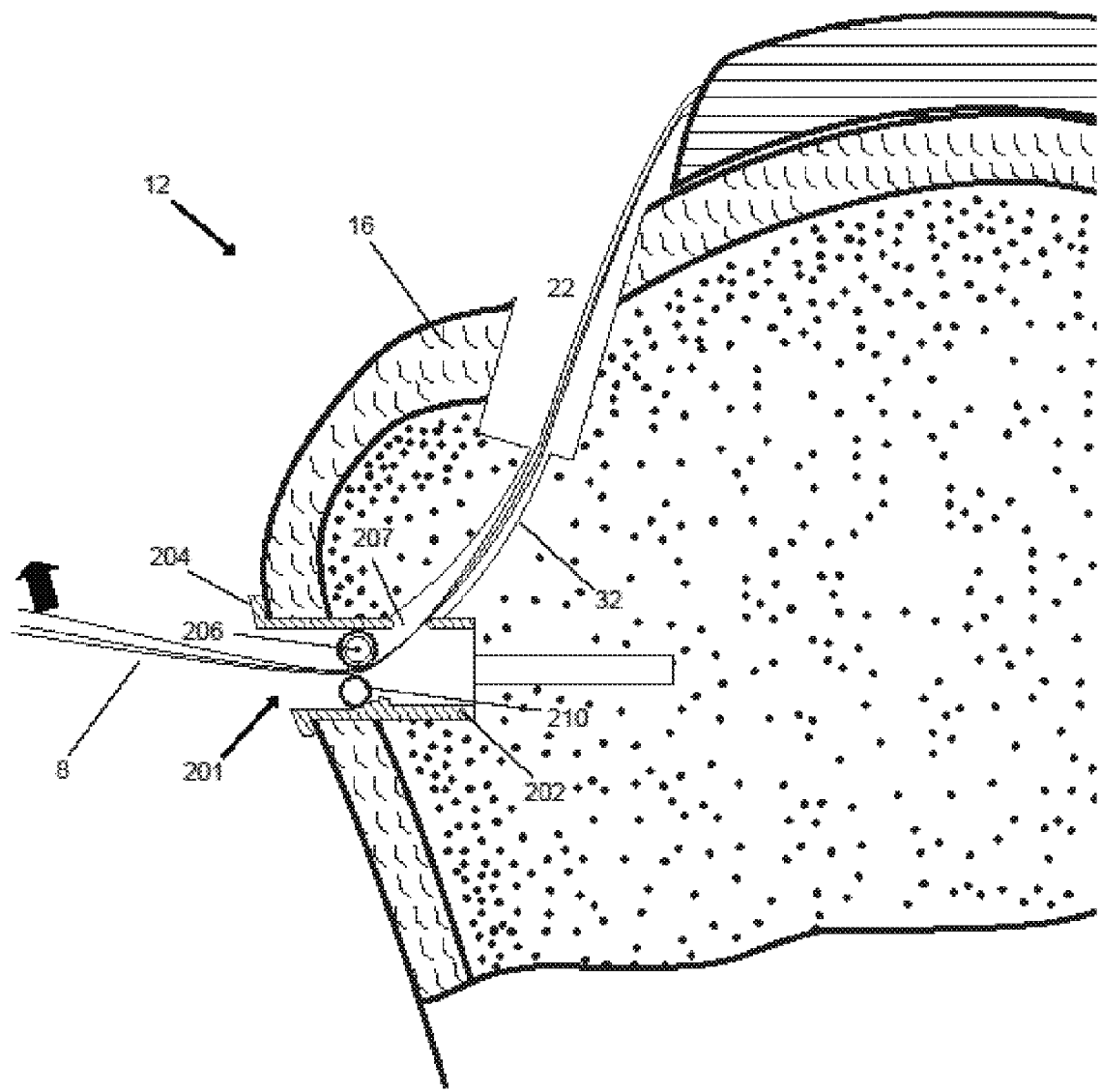
FIG. 18 illustrates the combination suture tensioning and securing device positioned in the humeral head depicted in FIG. 9.

In FIG. 18, tensioning and securing device 200 has been arthroscopically inserted into cavity 28 such that flange 204 abuts the lateral surface of humeral head 12. The free ends of sutures 8 were threaded through suture opening 207 distal of tensioning wheel 206, and then between tensioning wheel 206 and securing wheel 210 and out the lateral end of body 202 while sutures 8 and tensioning and securing device 200 were outside of the body. Once tensioning and securing device 200 is in place in the humeral head, sutures 8 are pulled in a direction lateral and upwards in relation to the humeral head, i.e. in the direction of the arrow. Pulling sutures 8 in this direction engages tensioning wheel 206, but releases (if tensioning and securing device 200 is in a secured position) or does not engage securing wheel 210. The surgeon may then continue to pull sutures 8 in the direction of the arrow to draw tendon 20 into trough 22. As mentioned previously, however, tendon 20 may be pre-positioned in trough 22 by pulling on sutures 8 before tensioning and securing device 100 has been inserted into cavity 28.

Figure 19:
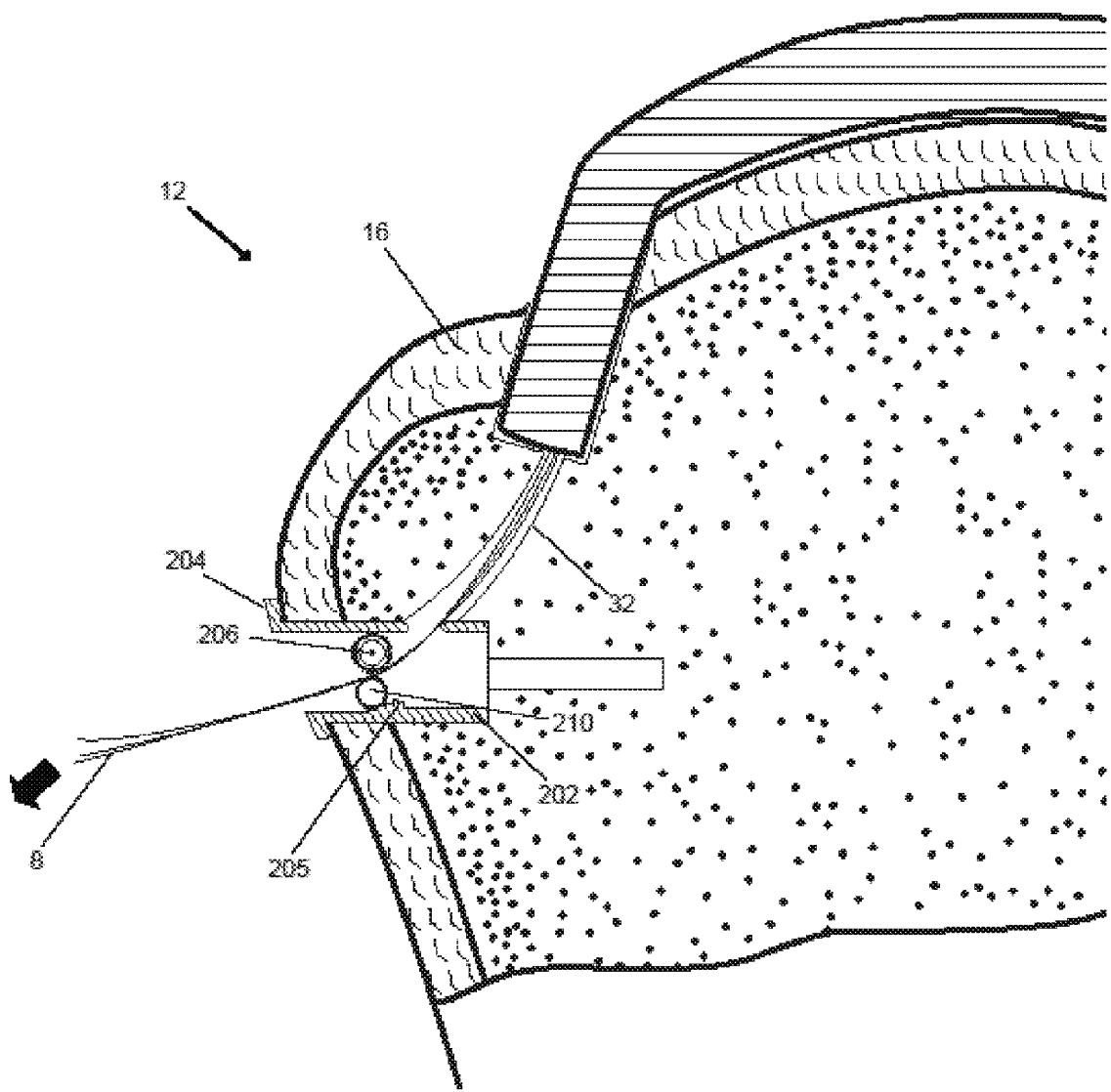
FIG. 19 illustrates the rotator cuff tendon drawn into the trough in the humeral head depicted in FIG. 18.

Once tendon 20 is in trough 22, the surgeon may pull sutures 8 in a direction lateral and downwards in relation to the humeral head, i.e. in the direction of the arrow in FIG. 19. This will pull sutures 8 into engagement with securing wheel 210 and apply slightly more than the desired final amount of tension to sutures 8. The surgeon then releases sutures 8, which will draw securing wheel 210 up body steps 205 and trap sutures 8 between tensioning wheel 206 and securing wheel 210.

Figure 20:
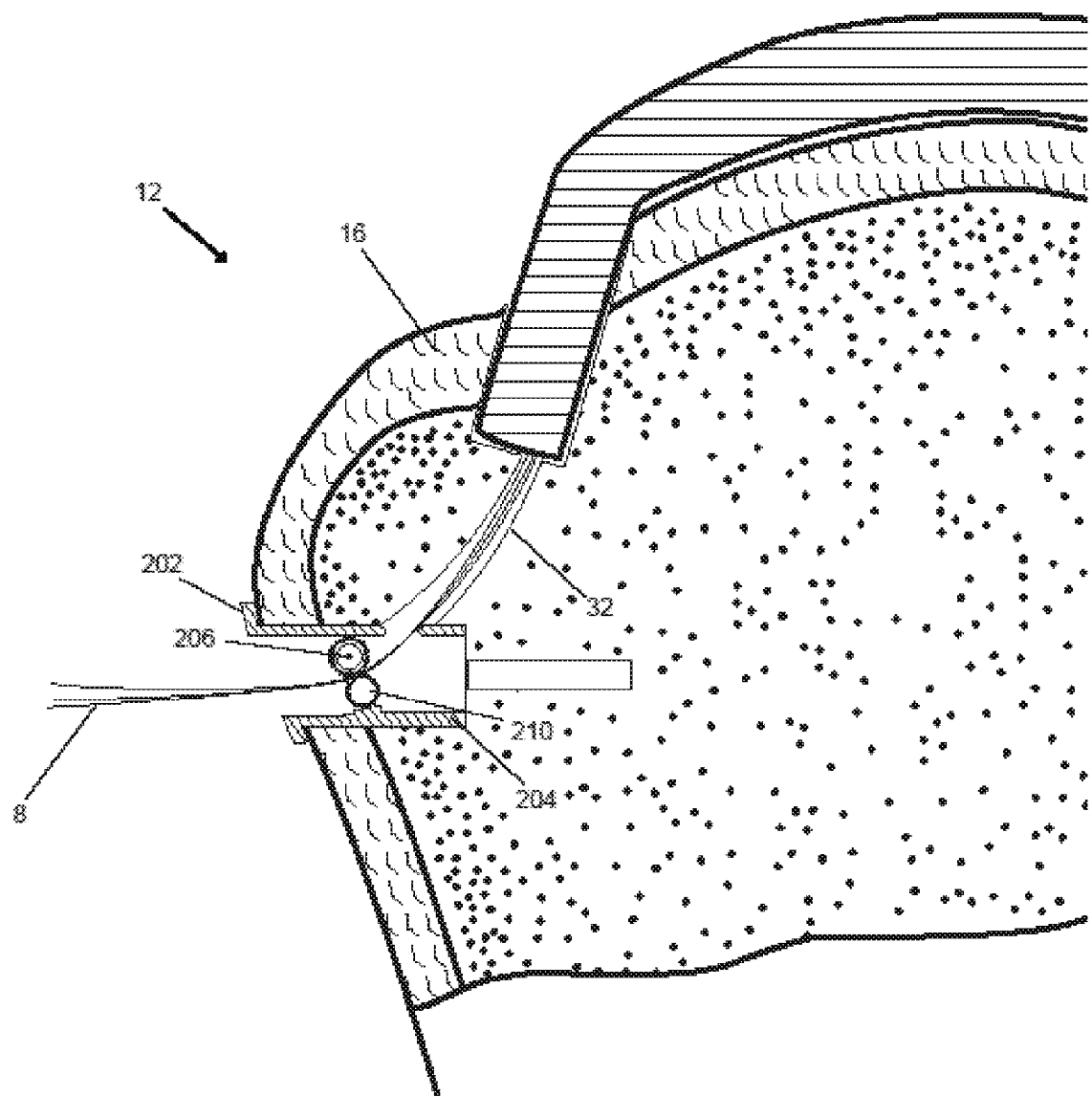
FIG. 20 illustrates the rotator cuff tendon in a secured position in the humeral head depicted in FIG. 19.

FIG. 20 shows tensioning and securing device 200 in this secured position. Tendon 20 will thus be held in place in trough 22 until biological healing between bone and tendon occurs. Excess suture material may be trimmed back inside tensioning and securing device 200. A cap 114 (see FIGS. 21-23) may be arthroscopically affixed over the lateral opening of tensioning and securing device 200 before closing the surgical portals. This cap 114 may be affixed in a variety of ways, including use of a threaded cap that engages threads in the lateral opening of body 102 (not shown), an interference fit, such as a snap fit, inside the lateral opening of body 102, cementing the cap 114 in place, etc. The cap 114 may also form a second securing point for sutures 8, employing any number of known methods of securing sutures or similar materials. For example, sutures 8 may be pulled under a prong on the cap 114 (not shown), or simply trapped between the cap 114 and body 202 if the cap 114 is snap fit or cemented in place (see FIG. 21), or threaded through a slit 116 in the cap 114 and secured by positioning the sutures 8 in a narrow portion of the slit 116 (see FIG. 22). The face of the cap may be comprised of a flexible material, including, but not limited to, surgical grade rubber for example. The flexibility of the face of cap 114 allows for movement of the sutures 8 to operate tensioning and securing device 200, for instance, while maintaining the lateral opening of tensioning and securing device 200 effectively closed off.

Figure 21:
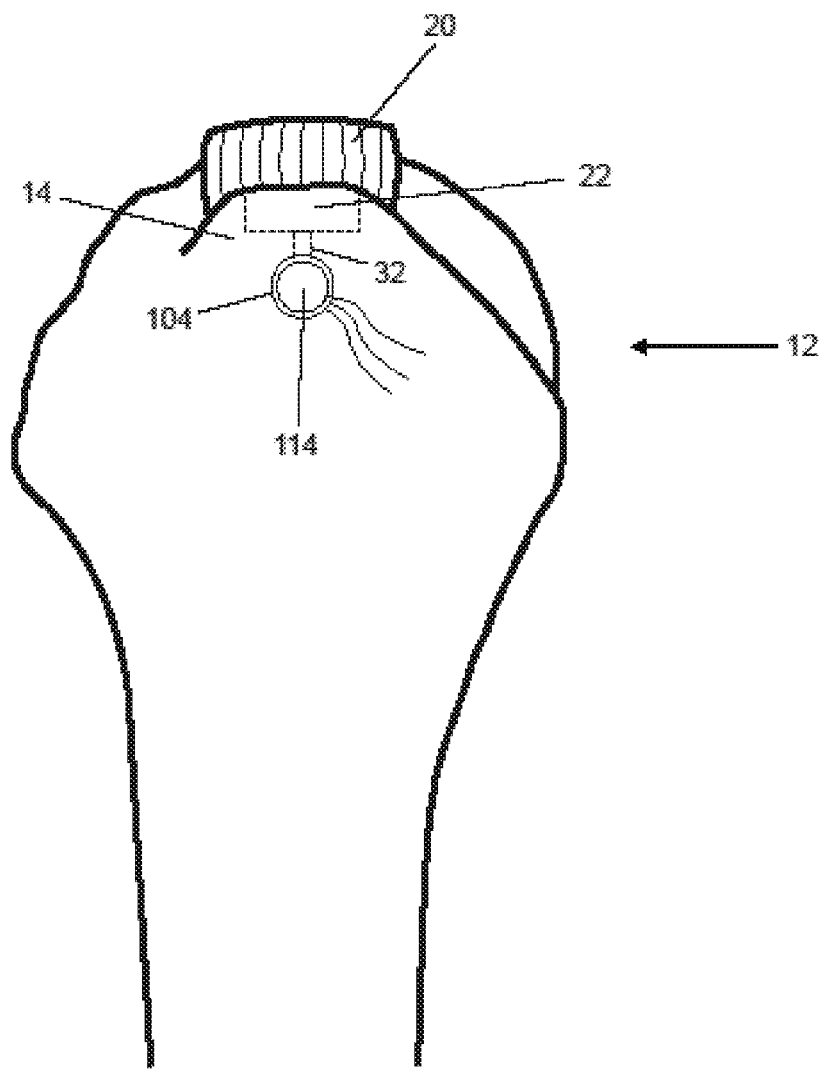
FIG. 21 illustrates a sagittal view of the upper portion of a humerus with a rotator cuff tendon affixed to the humerus using the present tensioning and securing device.
Figure 22:
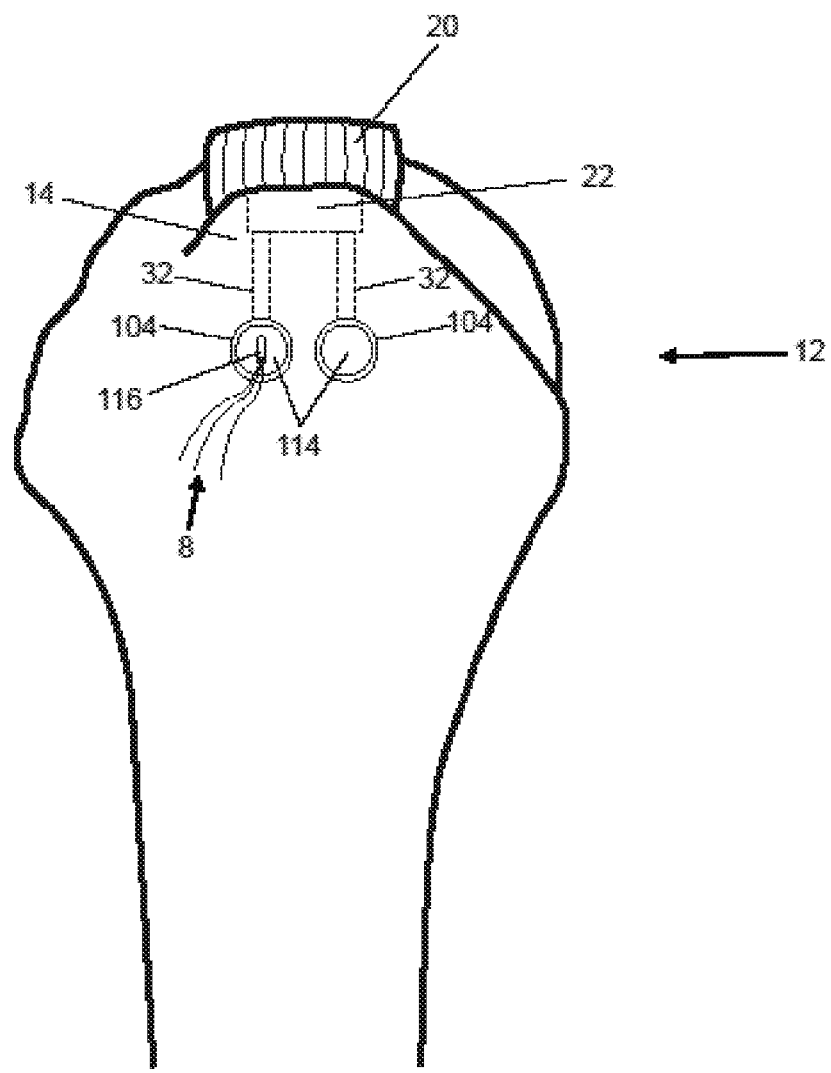
FIG. 22 illustrates a sagittal view of the upper portion of a humerus with a rotator cuff tendon affixed to the humerus using two tensioning and securing devices.
Figure 23:
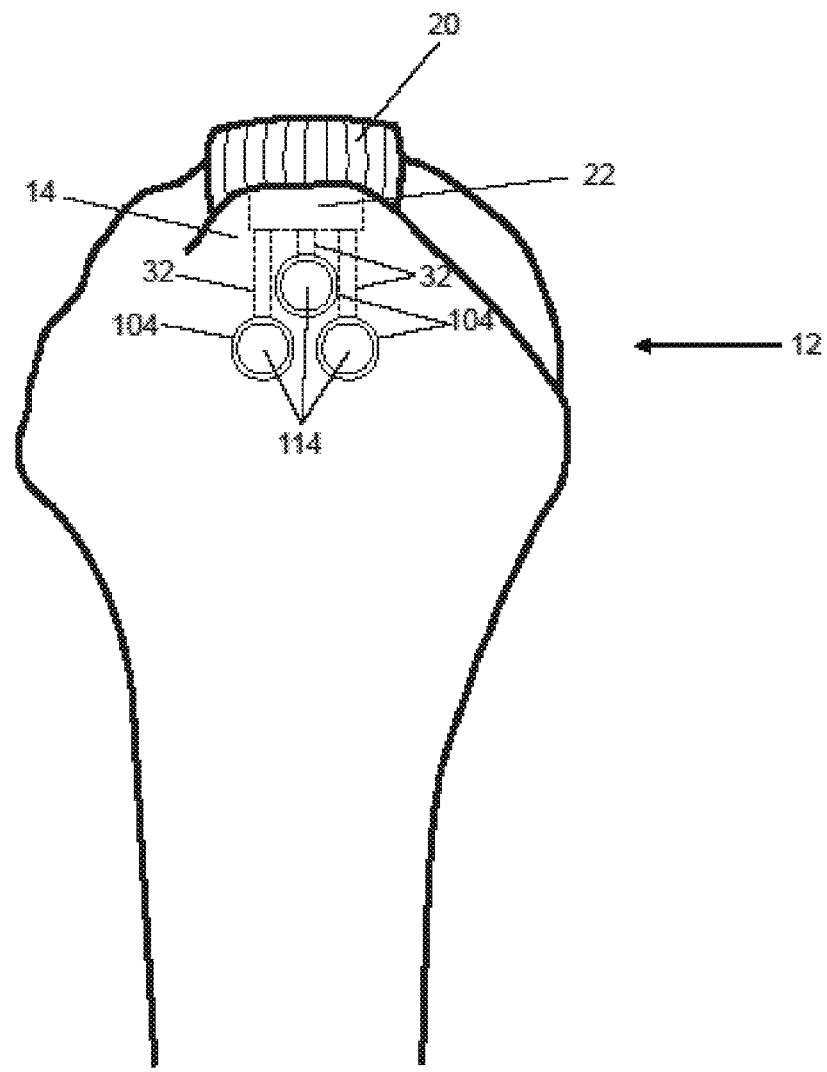
FIG. 23 illustrates a sagittal view of the upper portion of a humerus with a rotator cuff tendon affixed to the humerus using three tensioning and securing devices.

FIGS. 21-23 illustrate exemplary locations for tensioning and securing devices 101 or 201 on the surface of the humeral head 14. FIG. 21 depicts a single tunnel 32 and corresponding tensioning and securing device 100. In FIG. 22, a second tunnel 32 and corresponding tensioning and securing device 100 is added. Second tensioning and securing device 100 is shown positioned on the same plane as first tensioning and securing device 100. However, the devices may be on staggered planes as well. The surgeon can make this decision based upon an analysis of the bone structure and quality in order to minimize compromises in bone integrity. FIG. 23 adds yet another tunnel 32 and corresponding tensioning and securing device 100. Preferably the bone bridge between tensioning and securing devices will be equal to or greater than one centimeter.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. An adjustable tensioning and securing device for tensioning and securing a rotator cuff tendon to a humeral head, the tensioning and securing device comprising:
   a body, the body having an outer diameter, a proximal end and a distal end, a mounting section, and a suture opening lateral of the mounting section, the body sized to fit in a cavity created in a lateral section of a humeral head;
   a face member attached to the proximal end, the face member extending beyond the outer diameter of the body;
   a first arm, the first arm having, a base end and a securing end, the base end pivotally mounted to a first shaft attached to the mounting section;
   a second arm, the second arm having two side members and a center member, the second arm pivotally mounted at the side members to a second shaft attached to the first arm near a locking end;
   wherein rotating the second arm towards the proximal end of the body to contact the mounting section draws the securing end of the first arm such that the securing end of the first arm is moved toward, and into engagement with, the center member of the second arm to prevent movement of a suture or sutures located therebetween.

2. The adjustable tensioning and securing device of claim 1, wherein the body is circular in cross section.

3. The adjustable tensioning and securing device of claim 1, wherein the body is comprised of medical grade stainless steel.

4. The adjustable tensioning and securing device of claim 1, wherein the body is comprised of medical grade plastic.

5. The adjustable tensioning and securing device of claim 1, wherein the first arm, first shaft, second arm and second shaft are comprised of medical grade stainless steel.

6. The adjustable tensioning and securing device of claim 1, further comprising a cap configured to be arthroscopically affixed to an exposed end of the body when the adjustable tensioning and securing device is implanted.

7. The adjustable tensioning and securing device of claim 1, wherein the adjustable tensioning and securing device further comprises a cap.

8. The adjustable tensioning and securing device of claim 7, wherein the cap is further configured to secure the suture or sutures.

9. The adjustable tensioning and securing device of claim 1, wherein the body includes a hollow interior defined by a cylindrical wall, and the mounting section extends into the hollow interior of the body from an inner side of the wall and the suture opening extends through the wall.

* * * * *